United States Patent [19]

Zondler et al.

[11] Patent Number: 5,175,293
[45] Date of Patent: Dec. 29, 1992

[54] PESTICIDES

[75] Inventors: Helmut Zondler, Bottmingen; Adolf Hubele, Magden, both of Switzerland

[73] Assignee: Ciba-Geigy Corporation, Ardsley, N.Y.

[21] Appl. No.: 677,352

[22] Filed: Mar. 22, 1991

Related U.S. Application Data

[63] Continuation of Ser. No. 403,250, Sep. 5, 1989, abandoned.

[30] Foreign Application Priority Data

Sep. 9, 1988 [CH] Switzerland ............ 3371/88
Jul. 11, 1989 [CH] Switzerland ............ 2579/89

[51] Int. Cl.⁵ .................................. C07D 239/42
[52] U.S. Cl. ........................ 544/330; 544/331; 544/332
[58] Field of Search ............ 514/275; 544/330, 331, 544/332

[56] References Cited

U.S. PATENT DOCUMENTS 4,897,396 1/1990 Hubele .................. 514/275

FOREIGN PATENT DOCUMENTS 0019450 11/1980 European Pat. Off. .
0182190 5/1986 European Pat. Off. .
0270111 6/1988 European Pat. Off. .
2209470 9/1972 Fed. Rep. of Germany .
WO89/07599 8/1989 PCT Int'l Appl. .

*Primary Examiner*—John M. Ford
*Attorney, Agent, or Firm*—Marla J. Mathias; Edward McC. Roberts

[57] ABSTRACT

Compounds of the formula (I)

wherein:
$R_1$ is phenyl or phenyl mono- to tri-substituted by $R_4$; $R_2$ is hydrogen, $C_1$-$C_5$alkyl, $C_1$-$C_5$alkyl substituted by the radical $OR_5$ or by the radical $SR_5$, $C_3$-$C_6$cycloalkyl, $C_3$-$C_6$cycloalkyl mono- to tri-substituted by $C_1$-$C_4$alkyl or by halogen, $C_2$-$C_5$alkenyl, $C_2$-$C_5$alkynyl or the formyl radical; $R_3$ is hydrogen, $C_1$-$C_4$alkyl, $C_1$-$C_4$alkyl substituted by halogen, cyano or by the radical $OR_5$ or by the radical $SR_5$, $C_3$-$C_6$cycloalkyl or $C_3$-$C_6$cycloalkyl mono- to tri-substituted by $C_1$-$C_4$alkyl or by halogen; $R_4$ is halogen; $C_1$-$C_3$alkyl, $C_1$-$C_2$haloalkyl, $C_1$-$C_3$alkoxy or $C_1$-$C_3$haloalkoxy; $R_5$ is hydrogen, $C_1$-$C_5$alkyl, $C_3$-$C_5$alkenyl, $C_3$-$C_5$alkynyl or the radical $(CH_2)_n$-X-$C_1$-$C_3$-alkyl;
$R_7$ is the group -$NH_2$, $$-N=C\begin{matrix}R_8\\R_9\end{matrix} \quad \text{or} \quad -N\begin{matrix}R_{10}\\R_{11}\end{matrix};$$

and where $R_8$-$R_{11}$ are as defined hereafter.

12 Claims, No Drawings

PESTICIDES

This application is a continuation of application Ser. No. 403,250, filed Sep. 5, 1989, now abandoned.

The present invention relates to novel substituted 2-aminopyrimidine derivatives of formula I below. It also relates to the preparation of those compounds and to agrochemical compositions that contain at least one of those compounds as active ingredient. The invention relates also to the preparation of the said compositions and to the use of the compounds or the compositions for controlling pests, especially plant-destructive microorganisms, particularly fungi.

The pyrimidine compounds according to the invention have the general formula I

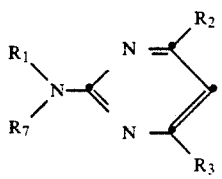

wherein: $R_1$ is phenyl or phenyl mono- to tri-substituted by $R_4$; $R_2$ is hydrogen, $C_1$-$C_5$alkyl, $C_1$-$C_5$alkyl substituted by the radical $OR_5$ or by the radical $SR_5$, $C_3$-$C_6$cycloalkyl, $C_3$-$C_6$cycloalkyl mono- to tri-substituted by $C_1$-$C_4$alkyl or by halogen, $C_2$-$C_5$alkenyl, $C_2$-$C_5$alkynyl or the formyl radical; $R_3$ is hydrogen, $C_1$-$C_4$alkyl, $C_1$-$C_4$alkyl substituted by halogen, cyano or by the radical $OR_5$ or by the radical $SR_5$, $C_3$-$C_6$cycloalkyl or $C_3$-$C_6$cycloalkyl mono- to tri-substituted by $C_1$-$C_4$alkyl or by halogen; $R_4$ is halogen, $C_1$-$C_3$alkyl, $C_1$-$C_2$haloalkyl, $C_1$-$C_3$alkoxy or $C_1$-$C_3$haloalkoxy; $R_5$ is hydrogen, $C_1$-$C_5$alkyl, $C_3$-$C_5$alkenyl, $C_3$-$C_5$alkynyl or the radical $(CH_2)_n$—X—$C_1$-$C_3$—alkyl;

$R_7$ is the group —$NH_2$,

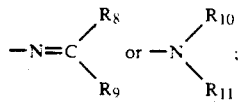

$R_8$ is hydrogen, $C_1$-$C_3$alkyl or $C_1$-$C_3$haloalkyl; $R_9$ is hydrogen, $C_1$-$C_8$alkyl, $C_1$-$C_3$alkyl substituted by hydroxy, $OR_{12}$, $SR_{12}$ or by $N(R_{12})_2$, $C_3$-$C_6$cycloalkyl, cyclopropyl substituted by $SR_{12}$, $C_3$-$C_{10}$alkenyl, $C_1$-$C_3$haloalkyl, phenyl, phenyl mono- to tri-substituted by halogen, $C_1$-$C_3$alkyl, $C_1$-$C_3$alkoxy, $C_1$-$C_3$haloalkoxy, $C_1$-$C_2$haloalkyl, hydroxy, nitro, cyano, amino or by dimethylamino, 1- or 2-naphthyl, 1-, 2- or 3-pyridyl,

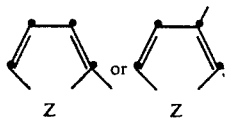

$R_8$ and $R_9$, together with the carbon atom in the radical $R_7$, are a saturated or unsaturated ring comprising 4 to 7 carbon atoms; $R_{10}$ is $CH(R_8)R_9$, phenyl, $C_3$-$C_5$alkenyl, $C_3$-$C_5$alkynyl or cyanoalkyl having 2 or 3 carbon atoms in the alkyl radical; $R_{11}$ is hydrogen, $C_1$-$C_5$alkyl, $C_3$-$C_5$alkenyl, $C_3$-$C_5$alkynyl or cyanoalkyl having 2 or 3 carbon atoms in the alkyl radical; $R_{12}$ is $CH_3$ or $C_2H_5$; X is oxygen or sulfur; Z is O, S, NH or $NCH_3$; and n is 1 to 3; including their acid addition salts and metal salt complexes.

Depending on the number of carbon atoms indicated, "alkyl" by itself or as a constituent of another substituent, such as haloalkyl, alkoxy or haloalkoxy, is to be understood as being, for example, methyl, ethyl, propyl, butyl or pentyl and isomers thereof, for example isopropyl, isobutyl, tert.-butyl or sec.-butyl. Halogen is fluorine, chlorine, bromine or iodine, preferably fluorine, chlorine or bromine. Haloalkyl and haloalkoxy are mono- to per-halogenated radicals, for example $CHCl_2$, $CH_2F$, $CCl_3$, $CH_2Cl$, $CHF_2$, $CF_3$, $CH_2CH_2Br$, $C_2Cl_5$, $CH_2Br$, $CHBrCl$ etc., preferably $CF_3$. Depending on the number of carbon atoms indicated, cycloalkyl is, for example, cyclopropyl, cyclobutyl, cyclopentyl or cyclohexyl.

The compounds of formula I are oils, resins or solids that are stable at room temperature and are distinguished by valuable microbicidal properties. They can be used preventively or curatively in the agricultural sector or related fields for controlling plant-destructive microorganisms. The compounds of formula I according to the invention, when used in low concentrations, are distinguished not only by excellent insecticidal and fungicidal activity but also by particularly good plant compatibility.

The invention relates both to the free compounds of formula I and to their addition salts with inorganic and organic acids and to their complexes with metal salts.

Salts according to the invention are especially addition salts with non-harmful inorganic or organic acids, for example hydrohalic acids, for example hydrochloric, hydrobromic or hydriodic acid, sulfuric acid, phosphoric acid, phosphorous acid, nitric acid or organic acids, such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid, 2-acetoxybenzoic acid or 1,2-naphthalene-disulfonic acid.

Metal salt complexes of formula I comprise the fundamental organic molecule and an inorganic or organic metal salt, for example the halides, nitrates, sulfates, phosphates, acetates, trifluoroacetates, trichloroacetates, propionates, tartrates, sulfonates, salicylates, benzoates, etc. of the elements of the second main group, such as calcium and magnesium, and of the third and fourth main groups, such as aluminium, tin or lead, and of the first to eighth sub-groups, such as chromium, manganese, iron, cobalt, nickel, copper, zinc, etc. The sub-group elements of the 4th period are preferred. The metals may be present in any of the various valencies attributed to them. The metal complexes may be mononuclear or polynuclear, that is to say, they may contain one or more organic molecular components as ligands.

Important groups of plant fungicides are compounds of formula I in which the symbols have the following meanings:

Group 1 (Substituents)

$R_1$ is phenyl or phenyl mono- to tri-substituted by $R_4$; $R_2$ is hydrogen, $C_1$-$C_5$alkyl, $C_1$-$C_5$alkyl substituted by the radical $OR_5$ or by the radical $SR_5$, $C_3$-$C_6$cycloalkyl, $C_3$-$C_6$cycloalkyl mono- to tri-substituted by $C_1$-$C_4$- alkyl or by halogen, $C_2$-$C_5$alkenyl, $C_2$-$C_5$alkynyl or the formyl radical; $R_3$ is $C_1$-$C_4$alkyl, $C_1$-$C_4$alkyl substituted by halogen, cyano or by the radical $OR_5$ or by the radical $SR_5$, $C_3$-$C_6$cycloalkyl or $C_3$-$C_6$cycloalkyl mono- to tri-substituted by $C_1$-$C_4$alkyl or by halogen; $R_4$ is halogen or $C_1$-$C_3$alkyl; $R_5$ is hydrogen, $C_1$-$C_5$alkyl, $C_3$-$C_5$alkenyl, $C_3$-$C_5$alkynyl or the radical $(CH_2)_n$—X—$C_1$-$C_3$alkyl; $R_9$ is hydrogen, $C_1$-$C_5$alkyl, $C_3$-$C_6$cycloalkyl, $C_3$-$C_5$alkenyl, $C_1$-$C_3$haloalkyl, phenyl or phenyl mono- to tri-substituted by halogen, methyl, methoxy, halomethoxy or by halomethyl; $R_8$ and $R_9$, together with the carbon atom in the radical $R_7$, are a saturated or unsaturated ring comprising 5 or 6 carbon atoms; $R_7$, $R_{10}$, $R_{11}$, $R_{12}$ and Z are as defined under formula I and halogen is preferably fluorine, chlorine or bromine, X is oxygen or sulfur; n is 1 to 3.

Group 2 (Substituents)

$R_1$ is phenyl or phenyl mono-substituted by halogen; $R_2$ is hydrogen, $C_1$-$C_5$alkyl, $C_1$-$C_5$alkyl substituted by $OR_5$, $C_3$-$C_6$cycloalkyl, $C_3$-$C_6$cycloalkyl mono- to tri-substituted by $C_1$-$C_4$alkyl or by halogen, $C_2$-$C_5$alkenyl, $C_2$-$C_5$alkynyl or the formyl radical; $R_3$ is $C_1$-$C_4$alkyl, $C_1$-$C_4$alkyl substituted by halogen, cyano or by $OR_5$, $C_3$-$C_6$cycloalkyl or $C_3$-$C_6$cycloalkyl substituted by methyl; $R_5$ is hydrogen or $C_1$-$C_2$alkyl; $R_9$ is hydrogen, $C_1$-$C_5$alkyl, $C_3$-$C_6$cycloalkyl, $C_3$-$C_5$alkenyl, $C_1$-$C_3$haloalkyl, phenyl or phenyl mono- to tri-substituted by halogen, methyl, methoxy, halomethoxy or by halomethyl; $R_8$ and $R_9$, together with the carbon atom in the radical $R_7$, are a saturated or unsaturated ring comprising 5 or 6 carbon atoms; $R_7$, $R_{10}$, $R_{11}$ and $R_{12}$ are as defined under formula I and halogen is preferably fluorine, chlorine or bromine.

Group 3 (Substituents)

$R_1$ is phenyl or phenyl mono- to tri-substituted by $R_4$; $R_2$ is hydrogen, $C_1$-$C_5$alkyl, $C_1$-$C_5$alkyl substituted by the radical $OR_5$ or by the radical $SR_5$, $C_3$-$C_6$cycloalkyl, $C_3$-$C_6$cycloalkyl mono- to tri-substituted by $C_1$-$C_4$alkyl or by halogen, $C_2$-$C_5$alkenyl, $C_2$-$C_5$alkynyl or the formyl radical; $R_3$ is $C_1$-$C_4$alkyl, $C_1$-$C_4$alkyl substituted by halogen, cyano or by the radical $OR_5$ or by the radical $SR_5$, $C_3$-$C_6$cycloalkyl or $C_3$-$C_6$cycloalkyl mono- to tri-substituted by $C_1$-$C_4$alkyl or by halogen; $R_4$ is halogen, $C_1$-$C_3$alkyl, $C_1$-$C_2$haloalkyl, $C_1$-$C_3$alkoxy or $C_1$-$C_3$haloalkoxy; $R_5$ is hydrogen, $C_1$-$C_5$ alkyl, $C_3$-$C_5$alkenyl, $C_3$-$C_5$alkynyl or the radical $(CH_2)_n$—X—$C_1$-$C_3$alkyl; $R_7$ is —$NH_2$; X is oxygen or sulfur; n is 1 to 3; including their acid addition salts and metal salt complexes.

Group 4 (Substituents)

$R_1$ is phenyl or phenyl mono- to tri-substituted by $R_4$; $R_2$ is hydrogen, $C_1$-$C_5$alkyl, $C_1$-$C_5$alkyl substituted by the radical $OR_5$ or by the radical $SR_5$, $C_3$-$C_6$cycloalkyl, $C_3$-$C_6$cycloalkyl mono- to tri-substituted by $C_1$-$C_4$alkyl or by halogen, $C_2$-$C_5$alkenyl, $C_2$-$C_5$alkynyl or the formyl radical; $R_3$ is $C_1$-$C_4$alkyl, $C_1$-$C_4$alkyl substituted by halogen, cyano or by the radical $OR_5$ or by the radical $SR_5$, $C_3$-$C_6$cycloalkyl or $C_3$-$C_6$cycloalkyl mono- to tri-substituted by $C_1$-$C_4$alkyl or by halogen; $R_4$ is halogen; $R_5$ is hydrogen, $C_1$-$C_5$alkyl, $C_3$-$C_5$alkenyl, $C_3$-$C_5$alkynyl or the radical $(CH_2)_n$—X—$C_1$-$C_3$alkyl; X is oxygen or sulfur; n is 1 to 3.

Group 5 (Substituents)

$R_1$ is phenyl or phenyl mono- to tri-substituted by halogen; $R_2$ is hydrogen, $C_1$-$C_5$alkyl, $C_1$-$C_5$alkyl substituted by the radical $OR_5$ or by the radical $SR_5$, $C_3$-$C_6$cycloalkyl, $C_3$-$C_6$cycloalkyl mono- to tri-substituted by $C_1$-$C_4$alkyl or by halogen, $C_2$-$C_5$alkenyl, $C_2$-$C_5$alkynyl or the formyl radical; $R_3$ is $C_1$-$C_4$alkyl, $C_1$-$C_4$alkyl substituted by halogen, cyano or by the radical $OR_5$ or by the radical $SR_5$, $C_3$-$C_6$cycloalkyl or $C_3$-$C_6$cycloalkyl mono- to tri-substituted by $C_1$-$C_4$alkyl or by halogen; $R_5$ is hydrogen, $C_1$-$C_5$alkyl, $C_3$-$C_5$alkenyl, $C_3$-$C_5$alkynyl or the radical $(CH_2)_n$—X—$C_1$-$C_3$alkyl; X is oxygen or sulfur; n is 1 to 3.

Group 6 (Substituents)

$R_1$ is phenyl or phenyl mono-substituted by chlorine or by fluorine; $R_2$ is $C_1$-$C_5$alkyl, or is $C_1$-$C_2$alkyl substituted by $OR_5$, $C_3$-$C_6$cycloalkyl, $C_3$-$C_6$cycloalkyl mono- to tri-substituted by $C_1$-$C_4$alkyl or by halogen, $C_2$-$C_5$alkenyl, $C_2$-$C_5$alkynyl or the formyl radical; $R_3$ is $C_1$-$C_4$alkyl, $C_1$-$C_4$haloalkyl, $C_3$-$C_6$cycloalkyl or $C_3$-$C_6$cycloalkyl substituted by methyl; $R_5$ is hydrogen or $C_1$-$C_2$alkyl.

Especially preferred are compounds of groups 5 and 6 wherein $R_3$ is: methyl, fluoromethyl, chloromethyl, bromomethyl, $C_3$-$C_6$cycloalkyl or methoxymethyl.

The following groups of individual compounds are preferred:

Group 1 (Compounds)

N-(4-fluoromethyl-6-cyclopropylpyrimid-2-yl)-N-phenylhydrazine;

N-(4-methyl-6-cyclopropylpyrimid-2-yl)-N-m-fluorophenylhydrazine;

N-(4-methyl-6-cyclopropylpyrimid-2-yl)-N-p-fluorophenylhydrazine;

Group 2 (Compounds)

N-(4-methyl-6-cyclopropylpyrimid-2-yl)-N-phenylhydrazine; N-(4,6-dimethylpyrimid-2-yl)-N-phenylhydrazine; N-(4-methyl-6-methoxymethylpyrimid-2-yl)-N-phenylhydrazine;

Group 3 (Compounds)

N-(4,6-dimethylpyrimid-2-yl)-N-phenylpropionaldehyde hydrazone; N-(4,6-dimethylpyrimid-2-yl)-N-phenylisobutyraldehyde hydrazone; N-(4-methyl-6-methoxymethylpyrimid-2-yl)-N-phenylisobutyraldehyde hydrazone; N-(4-methyl-6-methoxymethylpyrimid-2-yl)-N-phenylpropionaldehyde hydrazone; N-(4-methyl-6-cyclopropylpyrimid-2-yl)-N-phenylpropionaldehyde hydrazone; N-(4-methyl-6-cyclopropylpyrimid-2-yl)-N-phenyl-n-butyraldehyde hydrazone; N-(4-methyl-6-cyclopropylpyrimid-2-yl)-N-phenylisobutyraldehyde hydrazone; N-(4-methyl-6-cyclopropylpyrimid-2-yl)-N-phenyltrichloroacetaldehyde hydrazone; N-(4-methyl-6-cyclopropylpyrimid-2-yl)-N-p-fluorophenylacetaldehyde hydrazone; N-(4-methyl-6-cyclopropylpyrimid-2-yl)-N-p-fluorophenylisobutyraldehyde hydrazone; N-(4-methyl-6-cyclopropylpyrimid-2-yl)-N-m-fluorophenylisobutyraldehyde hydrazone; N-(4,6-dimethylpyrimid-2-yl)-N-phenyl-N'-methylhydrazine; N-(4,6-dimethylpyrimid-2-yl)-N-phenyl-N'-dimethylhydrazine; N-(4,6-dimethylpyrimid-2-yl)-N-phenyl-N'-n-propylhydrazine; N-(4,6-dimethylpyrimid-2-yl)-N-phenyl-N'-isobutylhydrazine; N-(4-methyl-6-methoxymethylpyrimid-2-yl)-N-phenyl-N'-methylhydrazine; N-(4-methyl-6-methoxymethylpyrimid-2-yl)-N-phenyl-N'-n-propylhydrazine; N-(4-methyl-6-methoxymethylpyrimid-2-yl)-N-phenyl-N'-dimethylhydrazine; N-(4-methyl-6-cyclopropylpyrimid- 2-yl)-N-phenyl-N'-methylhydrazine; N-(4-methyl-6-cyclopropylpyrimid-2-yl)-N-phenyl-N'-isobutylhydrazine; N-(4-methyl-6-cyclopropylpyrimid-2-yl)-N-phenyl-N'-dimethylhydrazine; N-(4-methyl-6-cyclopropylpyrimid-2-yl)-N-phenyl-N,-diethylhydrazine; N-(4-methyl-6-cyclopropylpyrimid-2-yl)-

N-phenyl-N'-methyl-N'-ethylhydrazine; N-(4-methyl-6-cyclopropylpyrimid-2-yl)-N-p-fluorophenyl-N'-ethylhydrazine; N-(4-methyl-6-methoxymethyl-pyrimid-2-yl)-N-m-fluorophenyl-N'-isopropylhydrazine.

The compounds of formula I are prepared as follows:

Process (a)

Reaction of a pyrimidine derivative of formula II

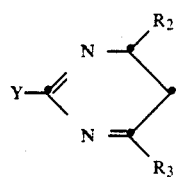

with a phenylhydrazine derivative of formula III

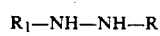

in the presence of a base, in an aprotic solvent and at temperatures of −50° to 150° C., preferably −30° to 80° C., wherein Y is halogen, preferably chlorine, the radical $SO_2R_6$ or $N^{\oplus}(CH_3)_3$, $R_6$ is $C_1$-$C_4$alkyl, phenyl or phenyl substituted by methyl or by chlorine and R is as defined for $R_{10}$ and $R_{11}$, and the latter and also $R_1$-$R_3$ are as defined under formula I.

Process (b)

Reaction of a pyrimidine hydrazine derivative of formula IV with an aldehyde or ketone of formula V to form a compound of formula VII with the removal of water

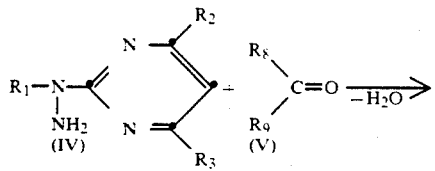

in any desired solvent, in the presence of an acid and at temperatures of −20° to 120° C., preferably 10° to 50° C., $R_1$-$R_3$ and $R_8$ and $R_9$ being as defined under formula I.

Azeotropic distillation or molecular sieves can be used to remove water from the reaction mixture. Drying agents, for example $CaCl_2$ or $Na_2SO_4$, can also be used. In the case of the reaction of derivative (Iv) with an aldehyde, the removal of water from the reaction mixture can often be dispensed with.

Process (c)

Reduction of a hydrazone derivative of formula VII

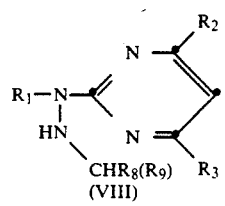

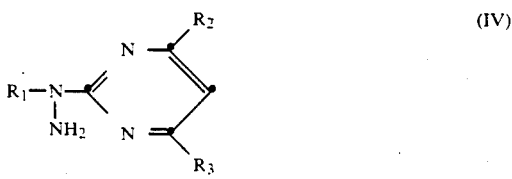

using a reducing agent, for example a borohydride etherate, $NaBH_4$, $NaCNBH_3$ or $LiAlH_4$, in an inert solvent, for example a suitable alcohol, tetrahydrofuran, dioxane, ethyl acetate or toluene, at temperatures of 0° to 50° C. or by catalytic hydrogenation using catalysts, for example nickel, platinum, palladium or rhodium.

Process (d)

Reductive alkylation of a pyrimidine hydrazine derivative of formula IV

with an aldehyde or ketone of formula V $$R_8-\overset{O}{\underset{\|}{C}}-R_9 \quad (V)$$

in the presence of a reducing agent, for example a borohydride etherate, $NaBH_4$, $NaCNBH_3$ or $LiAlH_4$, in an inert solvent, for example a suitable alcohol, tetrahydrofuran, dioxane, ethyl acetate or toluene, at temperatures of 0° to 50° C., preferably 10° to 40° C.

Process (e)

Alkylation of a pyrimidine hydrazine of formula IV or VIII with an alkyl halide $R_oHal$

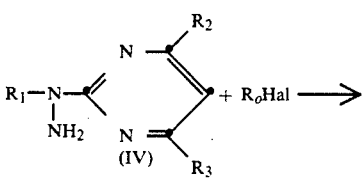

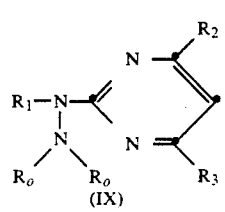

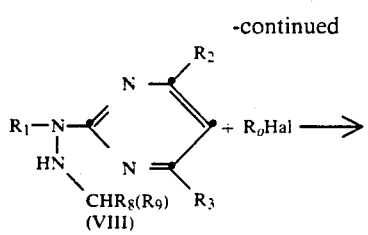

(VIII)

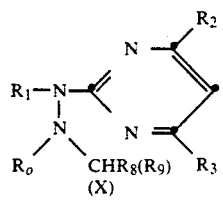

(X)

in an inert solvent, in the presence of a base and at temperatures of 0°–60° C., preferably 10°–40° C., $R_o$ being $C_1$–$C_4$alkyl. Other suitable alkylating agents are dialkyl sulfates.

In process (a–e) described above, $R_1$–$R_9$ are as defined under formula I.

In the processes described, it is possible, if necessary, to use both inorganic and organic bases, for example the following: the hydroxides, oxides or carbonates of lithium, sodium, potassium, magnesium, calcium, strontium and barium or, alternatively, hydrides, for example sodium hydride, and alcoholates, for example potassium tert.-butanolate, and tertiary amines, such as triethylamine, triethylenediamine or pyridine.

Solvents and diluents that may be used as reaction media in conformity with the particular reaction conditions are, for example, the following: aliphatic and aromatic hydrocarbons, such as benzene, toluene, xylenes, petroleum ether; halogenated hydrocarbons, such as chlorobenzene, methylene chloride, ethylene chloride, chloroform, carbon tetrachloride, tetrachloroethylene; ethers and ethereal compounds, such as dialkyl ethers (diethyl ether, diisopropyl ether, tert.-butyl methyl ether etc.), anisole, dioxane, tetrahydrofuran; nitriles, such as acetonitrile, propionitrile; N,N-dialkylated amides, such as dimethylformamide; and also mixtures of such solvents with one another.

The pyrimidine derivatives of formula II in which Y is halogen can be prepared according to known methods (see D. J. Brown, The Pyrimidines, Interscience Publishers, 1962).

An often-used method of synthesis consists in the condensation of urea with $\beta$-diketones to form 2-hydroxypyrimidines which are subsequently reacted to form 2-halopyrimidines as follows:

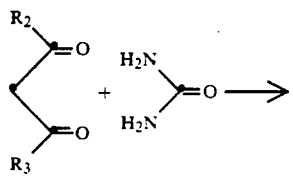

There may be used as halogenating agents especially phosphorus oxychloride or phosphorus oxybromide.

Another possible method of obtaining the 2-halopyrimidines of formula II is to prepare them by way of the 2-aminopyrimidines. The 2-aminopyrimidines are obtained by known methods (see D. J. Brown, The Pyrimidines, Interscience Publishers, 1962), then diazotised, and converted by the Sandmeyer process into the halopyrimidines. The 2-aminopyrimidines are obtained, for example, by condensing $\beta$-diketones with guanidine in the following manner.

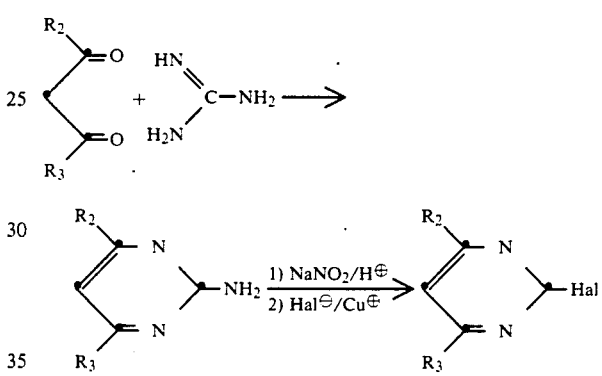

The pyrimidine derivatives of formula II in which Y is $SO_2$–$C_1$–$C_4$alkyl or $SO_2$aryl are obtained according to known methods by oxidising the corresponding alkyl or aryl mercaptopyrimidines, whose preparation is likewise known (see D. J. Brown, The Pyrimidines, Interscience Publishers, 1962).

Apart from the condensation of the corresponding diketones as described above, pyrimidines of formula II in which the radical $R_3$ is haloalkyl can also be obtained by reacting the hydroxyalkyl derivatives with phosphorus halide or thionyl halide in the presence of tertiary bases in inert solvents.

Some of the intermediates of formula II

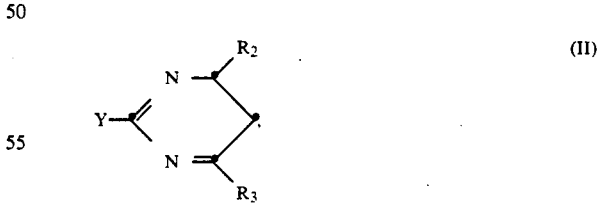

(II)

in which Y is halogen or $SO_2$–$R_6$ and $R_6$ is $C_1$–$C_4$alkyl or aryl and $R_2$ and $R_3$ are as defined under formula I, are known.

The following groups of compounds of formula II are novel:

1. Compounds wherein $R_2$ is $C_1$–$C_5$alkyl or $C_1$–$C_5$alkyl substituted by the radical $OR_5$ or by the radical $SR_5$; $R_3$ is $C_1$–$C_4$alkyl substituted by halogen, cyano or by the radical $OR_5$ or by the radical $SR_5$; $R_5$ is hydrogen, $C_1$–$C_5$alkyl, $C_3$–$C_5$alkenyl, $C_3$–$C_5$alkynyl or the radical $(CH_2)_n$—X—$C_1$-$C_3$alkyl; X is oxygen or sulfur; n is 1 to 3; Y is halogen, preferably chlorine, or $SO_2R_6$; and $R_6$ is $C_1$-$C_4$alkyl or aryl, with the exception of the compounds 2-chloro-4-methyl-6-methoxymethylpyrimidine and 2-chloro-4-methyl-6-trichloromethylpyrimidine.

2. Compounds wherein $R_2$ is hydrogen, $C_1$-$C_5$alkyl or $C_1$-$C_5$alkyl substituted by the radical $OR_5$ or by the radical $SR_5$; $R_3$ is $C_2$-$C_5$alkenyl or $C_2$-$C_5$alkynyl; $R_5$ is hydrogen, $C_1$-$C_5$alkyl, $C_3$-$C_5$alkenyl, $C_3$-$C_5$alkynyl or the radical $(CH_2)_n$—X—$C_1$-$C_3$alkyl; and Y is halogen.

The novel compounds of formula II form part of the present invention.

The hydrazine derivatives of formula III are known or can be prepared by methods known to the person skilled in the art.

Surprisingly, it has been found that the compounds of formula I have, for practical field application purposes, a very advantageous biocidal spectrum for the control of phytopathogenic microorganisms, especially fungi. They have very advantageous curative, preventive and, in particular, systemic properties, and can be used for protecting numerous cultivated plants. With the compounds of formula I it is possible to inhibit or destroy the pests which occur in plants or in parts of plants (fruit, blossoms, leaves, stems, tubers, roots) in different crops of useful plants, while at the same time the parts of plants which grow later are also protected, for example, from attack by phytopathogenic microorganisms.

The compounds of formula I are effective, for example, against the phytopathogenic fungi belonging to the following classes: *Fungi imperfecti* (especially Botrytis, and also Pyricularia, Helminthosporium, Fusarium, Septoria, Cercospora, Alternaria); and Basidiomycetes (e.g. Rhizoctonia, Hemileia, Puccinia). They are also effective against the Ascomycetes class (e.g. Venturia and Erysiphe, Podosphaera, Monilinia, Uncinula) and the Oomycetes class (e.g. Phytophthora, Pythium, Plasmopara). The compounds of formula I can also be used as dressing agents for protecting seeds (fruit, tubers, grains) and plant cuttings against fungus infections as well as against phytopathogenic fungi which occur in the soil. In addition, compounds of formula I are effective against insect pests, for example against pests on cereals, especially rice.

The invention also relates to compositions containing as active ingredient compounds of formula I, especially plant-protecting compositions, and to their use in the agricultural sector or related fields.

The present invention further embraces the preparation of those compositions, which comprises homogeneously mixing the active ingredient with one or more compounds or groups of compounds described herein. The invention furthermore relates to a method of treating plants, which comprises applying thereto the novel compounds of formula I or the novel compositions.

Target crops to be protected within the scope of the present invention comprise e.g. the following species of plants: cereals (wheat, barley, rye, oats, rice, maize, sorghum and related crops); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (cucumber, marrows, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor), or plants such as tobacco, nuts, coffee, sugar cane, tea, pepper, vines, hops, bananas and natural rubber plants, as well as ornamentals.

The compounds of formula I are normally applied in the form of compositions and can be applied to the crop area or plant to be treated, simultaneously or in succession, with further compounds. These compounds can be fertilisers or micronutrient donors or other preparations that influence plant growth. They can also be selective herbicides, insecticides, fungicides, bactericides, nematicides, molluscicides or mixtures of several of these preparations, if desired together with further carriers, surfactants or application-promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying a compound of formula I, or an agrochemical composition which contains at least one of said compounds, is foliar application. The number of applications and the rate of application depend on the risk of infestation by the corresponding pathogen. However, the compounds of formula I can also penetrate the plant through the roots via the soil (systemic action) if the locus of the plant is impregnated with a liquid formulation, or if the compounds are applied in solid form to the soil, e.g. in granular form (soil application). In paddy rice crops, such granulates may be applied in metered amounts to the flooded rice field. The compounds of formula I may, however, also be applied to seeds (coating) by impregnating the seeds either with a liquid formulation containing the active ingredient, or coating them with a solid formulation.

The compounds of formula I are used in unmodified form or, preferably, together with the adjuvants conventionally employed in the art of formulation, and are for this purpose advantageously formulated in known manner e.g. into emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}-C_{22}$), e.g. the sodium or potassium salts of oleic or stearic acid or of natural fatty acid mixtures which can be obtained e.g. from coconut oil or tallow oil. Mention may also be made of fatty acid methyllaurin salts.

More frequently, however, so-called synthetic surfactants are used, especially alkanesulfonates, fatty alcohol sulfates, sulfonated benzimidazole derivatives or alkylsulfonates.

The fatty alcohol sulfonates or sulfates are usually in the form of alkali metal salts, alkaline earth metal salts or unsubstituted or substituted ammonium salts and contain a $C_8-C_{22}$-alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethyleneethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8-C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ammonium bromide.

Further surfactants customarily employed in the art of formulation are known to the person skilled in the art or can be taken from the relevant specialist literature.

The agrochemical compositions usually contain 0.1 to 99% by weight, preferably 0.1 to 95% by weight, of a compound of formula I, 99.9 to 1% by weight, preferably 99.9 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also contain further auxiliaries such as stabilisers, antifoams, viscosity regulators, binders, tackifiers as well as fertilisers or other active ingredients for obtaining special effects.

The following Examples serve to illustrate the invention in more detail without limiting it.

1. Preparation Examples

Example 1.1

2-hydroxy-4-methyl-6-cyclopropyloyrimidine hydrochloride (starting material)

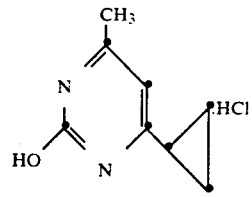

6.0 g (0.10 mol) of urea and 12.6 g (0.10 mol) of cyclopropylbutane-1,3-dione are dissolved at room temperature (~20° C.) in 35 ml of ethanol and 15 ml of 32% aqueous hydrochloric acid. After standing for 10 days at room temperature, the solution is concentrated using a rotary evaporator at a bath temperature of maximum 45° C. The residue is dissolved in 20 ml of ethanol; after a short time, the product begins to separate out in the form of the hydrochloride. 20 ml of diethyl ether are slowly added with stirring, the product is separated from the solvent by filtering off with suction and is washed with a mixture of diethyl ether and ethanol and dried at 60° C. in vacuo to give 7.14 g (38.2% of the theoretical yield) of 2-hydroxy-4-methyl-6-cyclopropylpyrimidine hydrochloride. The filtrate is concentrated and, after recrystallisation from 10 ml of ethanol and 20 ml of diethyl ether, a further 5.48 g (29.2% of the theoretical yield) of the title compound are obtained.

Analysis: C<sub>8</sub>H<sub>10</sub>N<sub>2</sub>O.HCl (mol. wt.: 186.64):

|   | % calc. | % found |
|---|---------|---------|
| C | 51.48   | 51.47   |
| H | 5.94    | 5.97    |
| N | 15.01   | 15.15   |
| Cl| 18.99   | 18.89   |

Example 1.2

2-chloro-4-methyl-6-cyclopropylpyrimidine hydrochloride (starting material)

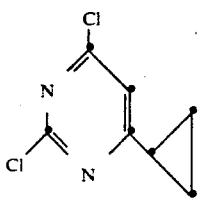

52.8 g (0.24 mol) of 2-hydroxy-4-methyl-6-cyclopropylpyrimidine hydrochloride are introduced into a mixture of 100 ml of phosphorus oxychloride and 117 g (0.79 mol) of diethylaniline and stirred; the exothermic reaction slowly begins, the temperature rising from room temperature to 63° C. The batch is then heated in an oil bath for 2 hours at 100°-110° C. internal temperature. After cooling to room temperature, the mixture is poured, with stirring, into a mixture of ice-water and methylene chloride. After one hour, the organic phase is separated in a separating funnel and is washed neutral with NaHCO<sub>3</sub> solution. After removing the solvent, 116.4 g of crude product comprising 2-chloro-4-methyl-6-cyclopropylpyrimidine and diethylaniline are obtained. Chromatographic separation using silica gel and a mixture of 25% ethyl acetate and 75% hexane as eluant affords 35.7 g (89.4% of the theoretical yield) of pure 2-chloro-4-methyl-6-cyclopropylpyrimidine in the form of a colourless oil.

Example 1.3

2-amino-4-diethoxymethyl-6-cyclopropyloyrimidine (starting material)

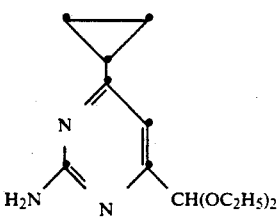

74.8 g (0.42 mol) of guanidine carbonate and 74.1 g (0.35 mol) of 4-cyclopropyl-2,4-dioxobutyraldehyde diethyl acetal are boiled for 10 hours in 250 ml of ethanol. The batch is then concentrated using a rotary evaporator and the residue is extracted with water and ethyl acetate. After evaporating the ethyl acetate, 79.2 g of crude product remain which are recrystallised from hexane to give 70.4 g (85.8% of the theoretical yield) of the pure title compound. M.p. 77°-78° C.

Example 1.4

2-chloro-4-formyl-6-cyclopropylpyrimidine (starting material)

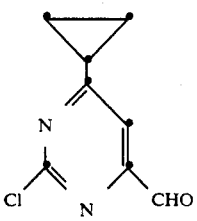

70.3 g (0.30 mol) of 2-amino-4-diethoxymethyl-6-cyclopropylpyrimidine are dissolved in 340 ml of 32% aqueous hydrochloric acid and cooled to −25° C. using dry ice. A solution of 40.9 g (0.59 mol) of sodium nitrite in 80 ml of water are then slowly added dropwise at −20° to −25° C., nitrogen evolving and a solid product separating out. After 2 hours the cooling means are removed and the mixture is allowed to rise to room temperature and is extracted with ethyl acetate. The extract is dried with sodium sulfate and the solvent is removed to give 21.9 g of crude product in the form of an oil. Further purification by means of column chromatography (silica gel, eluant 30 parts ethyl acetate and 70 parts hexane) affords 16.1 g of the pure title compound in the form of a colourless liquid. Refractive index $[n]_D^{25} = 1.5603$.

Analysis: C<sub>8</sub>H<sub>7</sub>ClN<sub>2</sub>O (mol. wt.: 182.61):

|   | % calc. | % found |
|---|---------|---------|
| C | 52.6    | 52.6    |
| H | 3.9     | 4.1     |
| N | 15.3    | 14.8    |
| Cl| 19.4    | 18.7    |

Example 1.5

2-chloro-4-hydroxymethyl-6-cyclooropylpyrimidine (starting material)

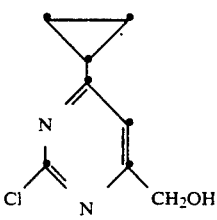

15.4 g (0.084 mol) of 2-chloro-4-formyl-6-cyclopropylpyrimidine are dissolved in 125 ml of methanol and reduced by the addition of 1.6 g of sodium borohydride. The batch is concentrated and extracted with ethyl acetate and the solvent is removed using a rotary evaporator to give 14.5 g of crude product which is recrystallised from a mixture of 20 ml of toluene and 20 ml of cyclohexane. The yield of the pure title compound is 13.7 g (88.4% of the theoretical yield); m.p. 102°-104° C.

Analysis: C<sub>8</sub>H<sub>9</sub>ClN<sub>2</sub>O (mol. wt.: 184.63):

|   | % calc. | % found |
|---|---|---|
| C | 52.04 | 52.05 |
| H | 4.91 | 4.90 |
| N | 15.17 | 15.27 |
| Cl | 19.20 | 19.28 |

Example 1.6
2-chloro-4-hydroxymethyl-6-cycloprooylpyrimidine methanesulfonate (starting material)

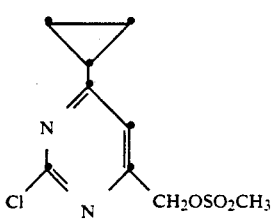

9.5 g (0.05 mol) of 4-hydroxymethylpyrimidine and 5.7 g of triethylamine are placed in 150 ml of tetrahydrofuran, and a solution of 6.5 g of methanesulfonic acid chloride in 30 ml of tetrahydrofuran is added dropwise with cooling. Triethylamine hydrochloride separates immediately and is filtered off with suction. Concentration yields 14.7 g of crude product which is chromatographed on silica gel (25 parts ethyl acetate and 75 parts hexane) to give 13.6 g of the pure title compound. M.p. 6420 -66° C.

Analysis: $C_9H_{11}ClN_2O_3S$ (mol. wt.: 262.71):

|   | % calc. | % found |
|---|---|---|
| C | 41.15 | 41.32 |
| H | 4.22 | 4.33 |
| N | 10.66 | 10.56 |
| S | 12.20 | 12.16 |

Example 1.7
2-chloro-4-fluoromethyl-6-cyclopropylpyrimidine (starting material)

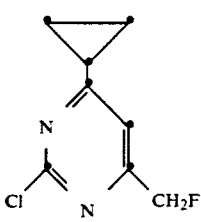

13.4 g (0.05 mol) of methanesulfonate are boiled under reflux for 5 hours in 70 ml of propionitrile with 9.4 g (0.16 mol) of potassium fluoride and 0.8 ml of 18-crown-6 as catalyst. Removal of the solvent and subsequent extraction with water and ethyl acetate gives a crude product which is purified by column chromatography (silica gel; 15 parts ethyl acetate and 85 parts hexane). The yield of the pure title compound is 7.5 g (78.6% of the theoretical yield); m.p. 37°–39° C.

Analysis: $C_8H_8ClFN_2$ (mol. wt.: 186.62):

|   | % calc. | % found |
|---|---|---|
| C | 51.49 | 51.73 |
| H | 4.32 | 4.45 |
| N | 15.01 | 14.90 |
| F | 10.18 | 10.26 |
| Cl | 19.00 | 18.50 |

Example 1.8
2-chloro-4-methyl-6-(2-methylcyclopropyl)-pyrimidine (starting material)

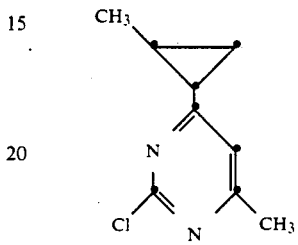

76.4 g (0.47 mol) of 2-amino-4-methyl-6-(2-methylcyclopropyl)-pyrimidine, produced by boiling guanidine carbonate with acetylmethyl-2-methylcyclopropyl ketone in ethanol, are dissolved in 536 g of 32% hydrochloric acid and cooled to −25° C. 2 g of copper powder are then added and a solution of 71.4 g (1.03 mol) of sodium nitrite in 200 ml of water is added dropwise at −25° C. over a period of 3 hours during which nitrogen and nitrous gases evolve. The mixture is then allowed to rise to room temperature, is extracted with ethyl acetate and the extracts are washed with water and dried with sodium sulfate. After removing the solvent, 27.7 g of crude product remain as residue which is purified by chromatography on silica gel with a mixture of 20 parts ethyl acetate and 80 parts hexane as eluant to give 32.2 g of the pure title compound; refractive index $[n]_D^{24}=1.5334$.

Analysis: $C_9H_{11}ClN_2$:

|   | % calc. | % found |
|---|---|---|
| C | 59.18 | 59.16 |
| H | 6.07 | 6.15 |
| N | 15.34 | 15.25 |
| Cl | 19.41 | 19.20 |

Example 1.9
2-(α-phenylhydrazino)-4,6-dimethylpyrimidine (Comp. 1.12)

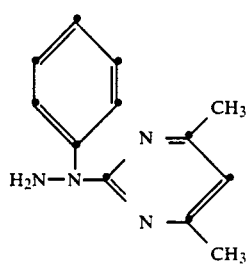

4.77 g (0.033 mol) of phenylhydrazine hydrochloride are suspended under nitrogen in 60 ml of tetrahydrofuran, and 7.41 g (0.066 mol) of potassium tert.-butanolate are added. A solution of 5.59 g (0.030 mol) of 2-methylsulfonyl-4,6-dimethylpyrimidine in 15 ml of tetrahydrofuran is then added dropwise at 25°-35° C. and, after 2 hours, the mixture is extracted with ethyl acetate and water with the addition of a small amount of acetic acid at pH6. After drying the organic phase with sodium sulfate and removing the solvent using a rotary evaporator, 5.88 g of crude product are obtained which are subjected to chromatographic purification using silica gel and a mixture of 35 parts ethyl acetate and 65 parts hexane to give 2.89 g of the pure title compound which, after recrystallisation from n-hexane, melts at 41°-43° C.

Example 1.10

2-(α-phenylhydrazino)-4,6-dimethylpyrimidine

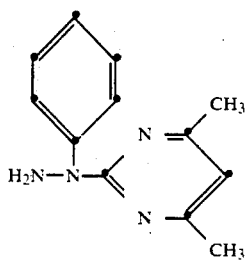

7.06 g (0.035 mol) of 2-trimethylammonium-4,6-dimethylpyrimidine chloride[1] and 5.78 g (0.04 mol) of phenylhydrazine hydrochloride are suspended in 50 ml of tetrahydrofuran, and a solution of 5.04 g (0.045 mol) of potassium tert.-butanolate in 25 ml of tetrahydrofuran is added dropwise under a nitrogen atmosphere. The exothermic reaction is maintained at 5°-10° C. by cooling. When the mixture has warmed to 20° C., it is extracted with ethyl acetate and water and the extract is dried with sodium sulfate. After concentration, 5.9 g of crude product are obtained which is purified by column chromatography (silica gel, eluant: mixture of 25 parts ethyl acetate and 75 parts hexane) to give 3.94 g of the pure title compound.
[1]W. Klötzer, Monatshefte f. Chemie 87, 131 (1956)

Example 1.11

N-(4-methyl-6-cyclopropyloyrimidin-2-yl)-N-phenylhydrazine (Comp. 1.4)

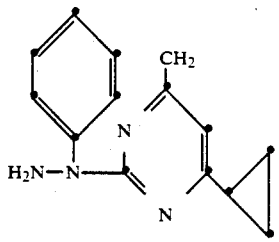

2.20 g (0.013 mol) of 2-chloro-4-methyl-6-cyclopropylpyrimidine and 1.62 g (0.015 mol) of phenylhydrazine are dissolved in 20 ml of tetrahydrofuran. A solution of 2.02 g (0.018 mol) of potassium tert.-butanolate in 20 ml of tetrahydrofuran is added dropwise to this solution with cooling at 20°-25° C. After 30 minutes, no further starting pyrimidine is detected by thin layer chromatography. The mixture is then extracted with water and ethyl acetate and, after removing the ethyl acetate using a rotary evaporator, 3.13 g of crude product are obtained which are purified by column chromatography on silica gel (eluant: 35% ethyl acetate/65% hexane). 2.83 g of the purified product are obtained (90.2% of the theoretical yield) which are recrystallised from a mixture of 8 ml of n-hexane and 1 ml of cyclohexane, affording 1.62 g of the title compound (m.p. 46° C.). The mother liquor is concentrated and is recrystallised again to give a further 0.42 g of that compound (m.p. 45°-46° C.). The total yield of the recrystallised compound is 2.04 g (65.3% of the theoretical yield).

Analysis: $C_{14}H_{16}N_4$ (mol. wt.: 240.31):

|   | % calc. | % found |
|---|---------|---------|
| C | 69.98   | 69.81   |
| H | 6.71    | 6.77    |
| N | 23.32   | 23.49   |

Example 1.12

(N-(4-methyl-6-cycloprooylpyrimidin-2-yl)-N-phenylisobutyraldehyde hydrazone (Comp. 3.26)

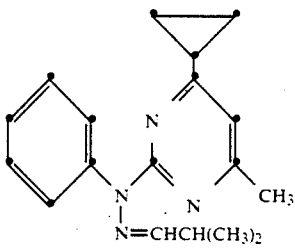

6.25 g (0.026 mol) of N-(4-methyl-6-cyclopropylpyrimidin-2-yl)-N-phenylhydrazine and 2.25 g (0.031 mol) of isobutyraldehyde are dissolved in 30 ml of methanol, producing a slightly exothermic reaction. After standing for two hours at room temperature, the solvent is removed using a rotary evaporator to give 7.8 g of crude product in the form of a viscous oil of which 3.2 g are purified by column chromatography on silica gel (eluant: 72% hexane/18% ethyl acetate/10% methanol). The yield is 2.92 g of the pure title compound having a melting point of 53°-55° C. This corresponds to a yield of 93% of the theoretical yield in terms of purification of all of the crude product.

Analysis: $C_{18}H_{22}N_4$ (mol. wt.: 294.40):

|   | % calc. | % found |
|---|---------|---------|
| C | 73.44   | 73.25   |
| H | 7.53    | 7.64    |
| N | 19.03   | 18.92   |

Example 1.13

N-(4-methyl-6-cyclopropylpyrimidin-2-yl)-N-phenyl-N'-isobutylhydrazine (Comp. 4.87)

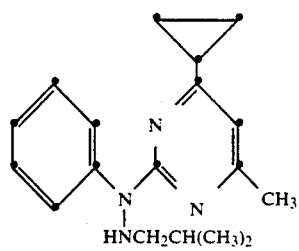

8.55 g (0.029 mol) of N-(4-methyl-6-cyclopropyl-pyrimidin-2-yl)-N-phenylisobutyraldehyde hydrazone are dissolved in 30 ml of methanol and 2 ml of glacial acetic acid. 2.14 g (0.029 mol) of sodium cyanoborohydride are then added in portions with stirring. The reaction proceeds exothermically; the temperature is maintained at 10°–15° C. by cooling. After 1 hour, the batch is worked up by extraction with ethyl acetate and water and the organic phase is concentrated using a rotary evaporator to give 8.5 g of crude product. Purification by column chromatography on silica gel (eluant: 85% hexane/15% ethyl acetate) affords 7.6 g (89% of the theoretical yield) of the title compound in the form of an oil having a refractive index of $[n]_D^{25} = 1.5733$.

Analysis: $C_{18}H_{24}N_4$ (mol. wt.: 296.42):

|   | % calc. | % found |
|---|---------|---------|
| C | 72.94   | 72.90   |
| H | 8.16    | 8.21    |
| N | 18.90   | 18.83   |

Example 1.14

N-(4-methyl-6-methoxymethylpyrimidin-2-yl)-N-phenyl-N'-methylhydrazine (Comp. 4.17)

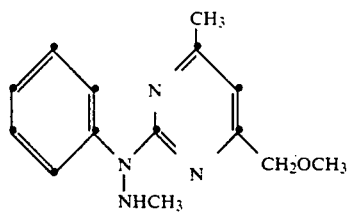

3.70 g (0.033 mol) of potassium tert.-butanolate are dissolved in 25 ml of tetrahydrofuran dried with molecular sieves, 3.67 g (0.03 mol) of N-methyl-N'-phenylhydrazine[2] are added and a solution of 4.22 g (0.025 mol) of 2-chloro-4-methyl-6-methoxymethylpyrimidine in 30 ml of anhydrous tetrahydrofuran is added dropwise under nitrogen at −20° C. to give a yellow-brown suspension which is gradually allowed to rise to room temperature. After 4 hours, the batch is extracted with water and ethyl acetate and the crude product is isolated by evaporating the solvent and purified by column chromatography on silica gel (eluant: 65% hexane/35% ethyl acetate). The pure title compound is obtained in the form of an oil having a refractive index of $[n]_D^{24} = 1.5793$.

[2] K. Kratzl. Monatshefte f. Chemie 89, 83 (1958) Analysis $C_{14}H_{18}N_4O$ (mol. wt.: 258.33)

|   | % calc. | % found |
|---|---------|---------|
| C | 65.09   | 65.08   |
| H | 7.02    | 7.09    |
| N | 21.69   | 21.05   |

Example 1.15

N-(4,6-dimethylpyrimidin-2-yl)-N-phenyl-N'-methylhydrazine (Comp. 4.1)

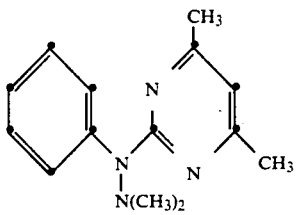

4.03 g (0.02 mol) of 2-trimethylammonium-4,6-dimethylpyrimidine hydrochloride[3] are stirred with 3.05 g (0.025 mol) of N-methyl-N'-phenylhydrazine under nitrogen in 30 ml of anhydrous tetrahydrofuran, and a solution of 3.36 g (0.03 mol) of potassium tert.-butanolate in 15 ml of tetrahydrofuran is added dropwise at room temperature. The batch is left overnight at room temperature to complete the reaction and is then extracted with water and ethyl acetate, the solvent is removed and the crude product is purified by column chromatography on silica gel (eluant: 70% hexane/30% ethyl acetate) to give 3.09 g of the title compound in the form of an oil.

[3] W. Klötzer. Monatshefte f. Chemie 87, 131 (1956)

Analysis $C_{13}H_{16}N_4$:

|   | % calc. | % found |
|---|---------|---------|
| C | 68.40   | 68.01   |
| H | 7.07    | 7.09    |
| N | 24.54   | 24.13   |

Example 1.16

N-(4,6-dimethylpyrimidin-2-yl)-N-phenyl-N'-dimethylhydrazine (Comp. 4.13)

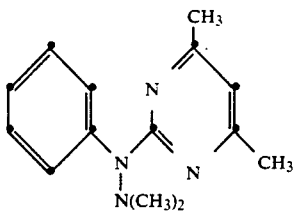

3.42 g (0.016 mol) of N-(4,6-dimethylpyrimidin-2-yl)-N-phenylhydrazine are dissolved in 20 ml of methanol together with 3.28 g (0.042 mol) of 38% formaldehyde and 2 ml of glacial acetic acid, and 1.33 g (0.018 mol) of sodium cyanoborohydride are added in portions at approximately 5° C. The reaction proceeds exothermically and is complete after one hour. The batch is extracted with ethyl acetate and water and the solvent is removed using a rotary evaporator to give 3.25 g of crude product which is purified by chromatography using silica gel and a mixture of 76% hexane, 19% ethyl acetate and 5% methanol to give 1.80 g (46.4% of the theoretical yield) of the pure title compound in the form of an oil; $[n]_D^{25} = 1.5673$.

Example 1.17

N-(4-methyl-6-cyclopropylpyrimidin-2-yl)-N-phenyl-N'-methyl-N'-isobutylhydrazine (Comp. 4.102)

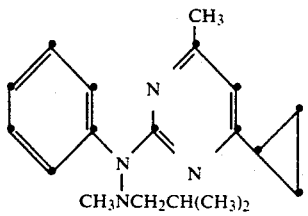

4.55 g (0.0153 mol) of N-(4-methyl-6-cyclopropylpyrimidin-2-yl)-N-phenyl-N'-isobutylhydrazine are dissolved with 1.45 g (0.0184 mol) of 38% formaldehyde in 25 ml of methanol and 2 ml of glacial acetic acid, and 1.24 g (0.0168 mol) of sodium cyanoborohydride are added in portions at 10° C. The reaction proceeds exothermically and, after one hour, the mixture is extracted with water and ethyl acetate. After removing the solvent, 4.95 g of crude product are obtained which is purified by column chromatography on silica gel (eluant: 85% hexane/15% ethyl acetate) to give 4.4 g of the title compound in the form of an oil; refractive index $[n]_D^{30} = 1.5613$.

Analysis: $C_{19}H_{26}N_4$ (mol. wt.: 310.45):

|   | % calc. | % found |
|---|---------|---------|
| C | 73.51   | 73.94   |
| H | 8.44    | 8.58    |
| N | 18.05   | 17.93   |

TABLE I

Compounds of formula

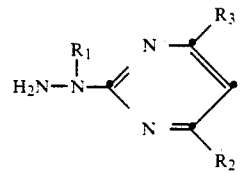

| Comp. No. | $R_1$ | $R_2$ | $R_3$ | physical constant |
|-----------|-------|-------|-------|-------------------|
| 1.1  | $C_6H_5$ | H | $CH_3$ | |
| 1.2  | $4\text{-}CF_3C_6H_4$ | $CH_3$ | $CH_3$ | |
| 1.3  | $4\text{-}F\text{-}C_6H_4$ | H | H | m.p. 129–131° C. |
| 1.4  | $C_6H_5$ | $CH_3$ | cyclopropyl | m.p. 45–46° C. |
| 1.5  | $C_6H_5$ | $C(CH_3)_3$ | $CH_2OCH_3$ | |
| 1.6  | $C_6H_5$ | $CH_2OCH_3$ | cyclopropyl | m.p. 37–38° C. |
| 1.7  | $C_6H_5$ | $CH_3$ | $CH_2OCH_3$ | m.p. 60–61° C. |
| 1.8  | $C_6H_5$ | $CH_2OC_2H_5$ | $C(CH_3)_3$ | |
| 1.9  | $C_6H_5$ | $CH_2OCH(CH_3)C_2H_5$ | $CH_3$ | |
| 1.10 | $3,4\text{-}(C_2H_5O)_2\text{-}C_6H_3$ | $CH_3$ | $CH_2OC_2H_5$ | |
| 1.11 | $C_6H_5$ | $CH_3$ | $CH_2OC_2H_5$ | |
| 1.12 | $C_6H_5$ | $CH_3$ | $CH_3$ | m.p. 41–43° C. |
| 1.13 | $4\text{-}CH_3O\text{-}C_6H_4$ | $C(CH_3)_3$ | $CH_2OC_2H_5$ | |
| 1.14 | $C_6H_5$ | $CH_3$ | $CHCl_2$ | |
| 1.15 | $3,5\text{-}Cl_2\text{-}C_6H_3$ | $CH_3$ | $CH_2OC_2H_5$ | |
| 1.16 | $3,5\text{-}Cl_2\text{-}C_6H_3$ | $CH_3$ | $CH_3$ | m.p. 154–156° C. |
| 1.17 | $3,5\text{-}Cl_2\text{-}C_6H_3$ | $C(CH_3)_3$ | $CH_2OC_2H_5$ | |
| 1.18 | $3,5\text{-}Cl_2\text{-}C_6H_3$ | cyclopropyl | $CH_2OCH_3$ | |
| 1.19 | $3,4\text{-}(C_2H_5O)_2\text{-}C_6H_3$ | $CH_2OC_2H_5$ | $C(CH_3)_3$ | |
| 1.20 | $4\text{-}CH_3O\text{-}C_6H_4$ | $CH_3$ | $CH_3$ | m.p. 90–92° C. |
| 1.21 | $4\text{-}CH_3O\text{-}C_6H_4$ | $CH_2OC_2H_5$ | $CH_3$ | |
| 1.22 | $3,4\text{-}(C_2H_5O)_2\text{-}C_6H_3$ | cyclopropyl | $CH_2OCH_3$ | |
| 1.23 | $C_6H_5$ | $CH_3$ | $CH_2OCH_2CH=CH_2$ | |
| 1.24 | $4\text{-}CH_3\text{-}C_6H_4$ | $CH_3$ | $CH_3$ | $n_D^{30}$ 1.604 |

TABLE I-continued

Compounds of formula

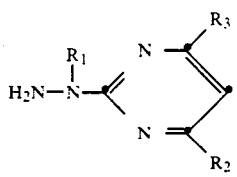

| Comp. No. | R₁ | R₂ | R₃ | physical constant |
|---|---|---|---|---|
| 1.25 | 4-OCH₃—C₆H₄ | △ (cyclopropyl) | CH₂OCH₃ | |
| 1.26 | 3,5-Cl₂—C₆H₃ | CH₃ | CH₂OCH(CH₃)C₂H₅ | |
| 1.27 | 4-OCH₃ | CH₃ | CH₂OCH(CH₃)C₂H₅ | |
| 1.28 | 2-Br—C₆H₄ | CH₃ | CH₃ | m.p. 55–57° C. |
| 1.29 | 3,5-Cl₂—C₆H₃ | CH₂OCH₂CH=CH₂ | CH₃ | |
| 1.30 | 4-CH₃O—C₆H₄ | C(CH₃)₃ | CH₂OCH₃ | |
| 1.31 | 3,5-Cl₂—C₆H₃ | CH₃ | CHCl₂ | |
| 1.32 | 3-Cl—C₆H₄ | CH₃ | CH₃ | m.p. 47–48° C. |
| 1.33 | 3,4-(C₂H₅O)₂—C₆H₃ | CH₃ | CH₂OCH(CH₃)C₂H₅ | |
| 1.34 | 4-CH₃O—C₆H₄ | CH₃ | CH₂OCH₃ | |
| 1.35 | 3,4-(C₂H₅O)₂—C₆H₃ | C(CH₃)₃ | CH₂OCH₃ | |
| 1.36 | 3,5-Cl₂—C₆H₃ | CH₃ | CH₂OCH₃ | |
| 1.37 | 2,4,6-Cl₃—C₆H₂ | CH₃ | CH₃ | m.p. 150–152° C. |
| 1.38 | 3,4-(C₂H₅O)₂—C₆H₃ | CH₃ | CH₂OCH₃ | |
| 1.39 | 3,5-Cl₂—C₆H₃ | CH₂OCH₂C≡CH | CH₃ | |
| 1.40 | C₆H₅ | CH₂OCH₂C≡CH | CH₃ | |
| 1.41 | 4-CH₃O—C₆H₄ | CH₂OCH₂C≡CH | CH₃ | |
| 1.42 | 3,5-(CF₃)₂—C₆H₃ | CH₃ | CH₃ | m.p. 88–90° C. |
| 1.43 | C₆H₅ | CH₂OCH₃ | CH₂OCH₃ | |
| 1.44 | C₆H₅ | CH₂SCH₃ | CH₃ | |
| 1.45 | C₆H₅ | CH₃ | CH(OCH₃)₂ | |
| 1.46 | C₆H₅ | CH₃ | CH(OC₂H₅)₂ | |
| 1.47 | C₆H₅ | ◇ (cyclobutyl) | CH₃ | |
| 1.48 | 4-Br—C₆H₄ | CH₃ | CH₃ | m.p. 92–93° C. |
| 1.49 | C₆H₅ | CH₃ | Cyclo-C₆H₁₁ | |
| 1.50 | C₆H₅ | CH₃ | CF₂Cl | |
| 1.51 | C₆H₅ | △ (cyclopropyl) | CF₃ | |
| 1.52 | C₆H₅ | △ (cyclopropyl) | △ (cyclopropyl) | |
| 1.53 | C₆H₅ | △ (cyclopropyl) | CF₂Cl | |
| 1.54 | 3-CH₃—C₆H₄ | CH₃ | CH₃ | m.p. 72–73° C. |
| 1.55 | C₆H₅ | C₂H₅ | △ (cyclopropyl) | $n_D^{25}$ 1.6063 |
| 1.56 | C₆H₅ | CH₃ | △—CH₃ (methylcyclopropyl) | $n_D^{30}$ 1.6072 |
| 1.57 | C₆H₅ | CH(CH₃)₂ | △ (cyclopropyl) | |
| 1.58 | C₆H₅ | CH₂OCH₃ | CF₃ | |
| 1.59 | C₆H₅ | △ (cyclopropyl) | CH(OCH₃)₂ | |
| 1.60 | C₆H₅ | CH₂OCH₃ | CH₂CH(CH₃)₂ | |

TABLE I-continued

Compounds of formula

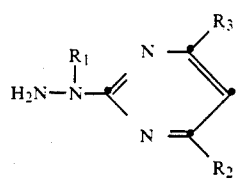

| Comp. No. | R₁ | R₂ | R₃ | physical constant |
|---|---|---|---|---|
| 1.61 | $C_6H_5$ | CHO | cyclopropyl | |
| 1.62 | $C_6H_5$ | $CH_2OCH_3$ | 1-methylcyclopropyl | |
| 1.63 | $C_6H_5$ | $CH_2CH_2CH_3$ | $CH_2OCH_3$ | |
| 1.64 | $C_6H_5$ | $CH(CH_3)_2$ | $CH_2OCH_3$ | |
| 1.65 | 4-F—$C_6H_4$ | $CH_3$ | 1-methylcyclopropyl | $n_D^{25}$ 1.5883 |
| 1.66 | $C_6H_5$ | $CH_2OH$ | cyclopropyl | |
| 1.67 | $C_6H_5$ | $(CH_2)_3CH_3$ | $CH_2OCH_3$ | |
| 1.68 | $C_6H_5$ | $C_2H_5$ | $CH_2OCH_3$ | $n_D^{24}$ 1.5923 |
| 1.69 | $C_6H_5$ | $CH_2OCH_3$ | 1-chlorocyclopropyl | |
| 1.70 | $C_6H_5$ | $CH_2OCH_3$ | $CF_2Cl$ | |
| 1.71 | $C_6H_5$ | cyclopropyl | $CH_2Cl$ | |
| 1.72 | $C_6H_5$ | $CH_2OCH_3$ | $CH(OCH_3)_2$ | |
| 1.73 | 4-F—$C_6H_4$ | $CH_3$ | $CH_3$ | m.p. 78–79° C. |
| 1.74 | 4-Cl—$C_6H_4$ | $CH_3$ | $CH_3$ | m.p. 101–102° C. |
| 1.75 | 4-F—$C_6H_4$ | $CH_3$ | $C_2H_5$ | $n_D^{25}$ 1.5723 |
| 1.76 | $C_6H_5$ | cyclopropyl | $CHCl_2$ | |
| 1.77 | $C_6H_5$ | cyclopropyl | $CH_2Br$ | |
| 1.78 | $C_6H_5$ | $CH_2OCH_3$ | $CF_2CF_3$ | |
| 1.79 | $C_6H_5$ | cyclopropyl | $CH_2F$ | $n_D^{32}$ 1.6150 |
| 1.80 | $C_6H_5$ | $CH(CH_3)C_2H_5$ | $CH_2OCH_3$ | |
| 1.81 | $C_6H_5$ | CHO | $CH_2OCH_3$ | |
| 1.82 | $C_6H_5$ | $(CH_2)_3CH_3$ | cyclopropyl | |
| 1.83 | $C_6H_5$ | $(CH_2)_2CH_3$ | cyclopropyl | |
| 1.84 | $C_6H_5$ | cyclopropyl | $CH(CH_3)C_2H_5$ | |

TABLE I-continued

Compounds of formula

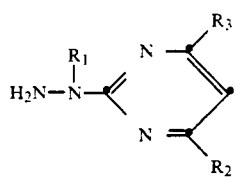

| Comp. No. | R₁ | R₂ | R₃ | physical constant |
|---|---|---|---|---|
| 1.85 | $C_6H_5$ | cyclopropyl | $CH_2CH(CH_3)_2$ | |
| 1.86 | $C_6H_5$ | 2,2-Cl₂-1-CH₃-cyclopropyl | cyclopropyl | |
| 1.87 | $4\text{-}CF_3\text{-}C_6H_4$ | $CH_3$ | $CH_2OCH_3$ | |
| 1.88 | $4\text{-}Br\text{-}C_6H_4$ | $CH_3$ | $CH_2OCH_3$ | |
| 1.89 | $C_6H_5$ | $CH_2OH$ | $CH_2OCH_3$ | |
| 1.90 | $C_6H_5$ | cyclopropyl | $CF_2CF_3$ | |
| 1.91 | $C_6H_5$ | $CH_2OCH_3$ | $CH_2Cl$ | |
| 1.92 | $4\text{-}CH_3\text{-}C_6H_4$ | $CH_2OCH_3$ | $CH_3$ | |
| 1.93 | $C_6H_5$ | $CH(OC_2H_5)_2$ | cyclopropyl | $n_D^{25}$ 1.5763 |
| 1.94 | $2\text{-}CF_3\text{-}C_6H_4$ | $CH_3$ | $CH_2OCH_3$ | |
| 1.95 | $C_6H_5$ | $CH_3$ | 2,2-Cl₂-1-CH₃-cyclopropyl | |
| 1.96 | $C_6H_5$ | $CH_3$ | $CHO$ | |
| 1.97 | $C_6H_5$ | cyclopropyl | 1-CH₃-cyclopropyl | |
| 1.98 | $4\text{-}Cl\text{-}C_6H_4$ | $CH_3$ | $CH_2OCH_3$ | |
| 1.99 | $4\text{-}Cl\text{-}3\text{-}CF_3\text{-}C_6H_3$ | $CH_3$ | $CH_2OCH_3$ | |
| 1.100 | $3\text{-}CH_3\text{-}C_6H_4$ | $CH_3$ | $CH_2OCH_3$ | |
| 1.101 | $3\text{-}F\text{-}C_6H_4$ | $CH_3$ | $CH(OC_2H_5)_2$ | |
| 1.102 | $3\text{-}CF_3\text{-}C_6H_4$ | $CH_2OCH_3$ | $CH_3$ | |
| 1.103 | $3\text{-}Cl\text{-}C_6H_4$ | $CH_2OCH_3$ | $CH_3$ | |
| 1.104 | $3\text{-}F\text{-}C_6H_4$ | $CH_2OCH_3$ | $CH_3$ | $n_D^{24}$ 1.5863 |
| 1.105 | $4\text{-}F\text{-}C_6H_4$ | $CH_2OCH_3$ | $CH_3$ | m.p. 70–72° C. |
| 1.106 | $4\text{-}Cl\text{-}C_6H_4$ | $CH_3$ | cyclopropyl | |
| 1.107 | $C_6H_5$ | $CH_3$ | $CH_2OH$ | |
| 1.108 | $4\text{-}F\text{-}C_6H_4$ | $CH_3$ | cyclopropyl | m.p. 93–95° C. |
| 1.109 | $C_6H_5$ | $CH_2OCH_3$ | $CH_2Br$ | |
| 1.110 | $C_6H_5$ | $CH_3$ | $CH_2Cl$ | |
| 1.111 | $4\text{-}Cl\text{-}3\text{-}CF_3\text{-}C_6H_3$ | cyclopropyl | $CH_3$ | |
| 1.112 | $C_6H_5$ | $CH_2OCH_3$ | $CH_2F$ | |

TABLE I-continued

Compounds of formula

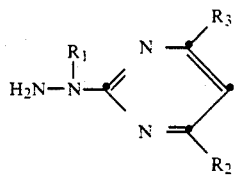

| Comp. No. | $R_1$ | $R_2$ | $R_3$ | physical constant |
|---|---|---|---|---|
| 1.113 | $C_6H_5$ | ◁ | ◁–$CH_3$ | |
| 1.114 | $C_6H_5$ | $CH_3$ | $CH_2Br$ | |
| 1.115 | $C_6H_5$ | $CH_3$ | $CH_2F$ | |
| 1.116 | $C_6H_5$ | $C(CH_3)_3$ | $C(CH_3)_3$ | |
| 1.117 | $C_6H_5$ | $(CH_2)_4CH_3$ | $CH_3$ | |
| 1.118 | $C_6H_5$ | $C_2H_5$ | $C_2H_5$ | $n_D^{25}$ 1.5923 |
| 1.119 | $C_6H_5$ | $CH_3$ | $C_2H_5$ | $n_D^{30}$ 1.5953 |
| 1.120 | $C_6H_5$ | $CH_3$ | $C{\equiv}CH$ | |
| 1.121 | $C_6H_5$ | $CH_3$ | $C{\equiv}CCH_3$ | |
| 1.122 | 3-F—$C_6H_4$ | $CH_3$ | ◁ | m.p. 41–42° C. |
| 1.123 | 3-F—$C_6H_4$ | ◁ | $CH_2F$ | |
| 1.124 | 3-F—$C_6H_4$ | $CH_3$ | ◁–$CH_3$ | $n_D^{25}$ 1.5943 |
| 1.125 | $C_6H_5$ | H | ◁ | |
| 1.126 | $C_6H_5$ | $CH_2CH_2CH(CH_3)_2$ | $CH_3$ | |
| 1.127 | 4-F—$C_6H_4$ | $C_2H_5$ | $C_2H_5$ | $n_D^{25}$ 1.5743 |
| 1.128 | 4-F—$C_6H_4$ | $CH_2OCH_3$ | ◁ | m.p. 56–57° C. |
| 1.129 | 3-F—$C_6H_4$ | $CH_3$ | $CH_3$ | m.p. 60–62° C. |
| 1.130 | 3-F—$C_6H_4$ | $CH_3$ | $C_2H_5$ | $n_D^{30}$ 1.5873 |
| 1.131 | 3-F—$C_6H_4$ | $CH_2OCH_3$ | ◁ | $n_D^{25}$ 1.5873 |
| 1.132 | $C_6H_5$ | $CH_3$ | $CF_3$ | $n_D^{24}$ 1.5543 |
| 1.133 | 4-F—$C_6H_4$ | $CH_2OCH_3$ | $C_2H_5$ | $n_D^{24}$ 1.5733 |
| 1.134 | 2-F—$C_6H_4$ | $CH_3$ | $CH_3$ | $n_D^{23}$ 1.5863 |
| 1.135 | 2-F—$C_6H_4$ | $CH_3$ | $CH_2OCH_3$ | $n_D^{23}$ 1.5773 |
| 1.136 | 2-F—$C_6H_4$ | $CH_3$ | ◁ | $n_D^{37}$ 1.5811 |
| 1.137 | 4-F—$C_6H_4$ | $C_2H_5$ | ◁ | $n_D^{22}$ 1.5813 |
| 1.138 | 3-F—$C_6H_4$ | $C_2H_5$ | ◁ | $n_D^{23}$ 1.5894 |
| 1.139 | $C_6H_5$ | $CH_2CH_2CH_3$ | $CH_2CH_2CH_3$ | $n_D^{23}$ 1.5743 |
| 1.140 | 3-F—$C_6H_4$ | $CH_2CH_2CH_3$ | $CH_2CH_2CH_3$ | $n_D^{23}$ 1.5633 |
| 1.141 | 2-F—$C_6H_4$ | ◁–$CH_3$ | $CH_3$ | $n_D^{24}$ 1.5854 |

TABLE 1-continued

Compounds of formula

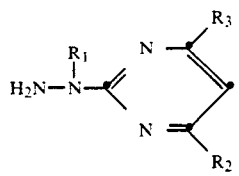

| Comp. No. | $R_1$ | $R_2$ | $R_3$ | physical constant |
|---|---|---|---|---|
| 1.142 | $C_6H_5$ | H | H | m.p. 75–77° C. |

TABLE 2

Compounds of formula

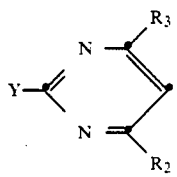

| Comp. No. | $R_2$ | $R_3$ | Y | physical constant |
|---|---|---|---|---|
| 2.1 | CHO | cyclo-C$_3$H$_5$ | Cl | $n_D^{25}$ 1.5603 |
| 2.2 | t-butyl | $CH_2OC_2H_5$ | Cl | |
| 2.3 | $CH_3$ | $CH_2OCH(CH_3)C_2H_5$ | Cl | |
| 2.4 | $CH_3$ | $CH_2OC_2H_5$ | Cl | |
| 2.5 | $CH_3$ | $CHCl_2$ | Cl | |
| 2.6 | $CH_3$ | $CH_2OCH_2CH=CH_2$ | Cl | |
| 2.7 | $CH_3$ | $CH_2OCH_2C\equiv CH$ | Cl | |
| 2.8 | $CH_2OCH_3$ | $CH_2OCH_3$ | Cl | |
| 2.9 | $CH_2OCH_3$ | cyclo-C$_3$H$_5$ | Cl | $n_D^{25}$ 1.5344 |
| 2.10 | $CH_3$ | $CH(OCH_3)_2$ | Cl | |
| 2.11 | $CH_3$ | $CH(OC_2H_5)_2$ | Cl | |

TABLE 2-continued

Compounds of formula

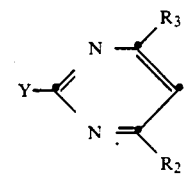

| Comp. No. | $R_2$ | $R_3$ | Y | physical constant |
|---|---|---|---|---|
| 2.12 | $CH_3$ | $CF_2Cl$ | Cl | |
| 2.13 | $CH_2OCH_3$ | $CF_3$ | Cl | |
| 2.14 | $CH(OC_2H_5)_2$ | cyclo-C$_3$H$_5$ | Cl | oil |
| 2.15 | n-propyl | $CH_2OCH_3$ | Cl | |
| 2.16 | iso-propyl | $CH_2OCH_3$ | Cl | |
| 2.17 | n-butyl | $CH_2OCH_3$ | Cl | |
| 2.18 | $CH_2OCH_3$ | $C_2H_5$ | Cl | $n_D^{24}$ 1.5064 |
| 2.19 | $CH_2OCH_3$ | $CH(OCH_3)_2$ | Cl | |
| 2.20 | $CH_2OCH_3$ | $CF_2CF_3$ | Cl | |
| 2.21 | $CH_2OH$ | $CH_2OCH_3$ | Cl | |
| 2.22 | $CH_2OCH_3$ | $CH_2Cl$ | Cl | |
| 2.23 | $CH_2OCH_3$ | $CH_2F$ | Cl | |
| 2.24 | $CH_3$ | $CH_2OCH_3$ | $SO_2CH_3$ | |

TABLE 3

Compounds of formula

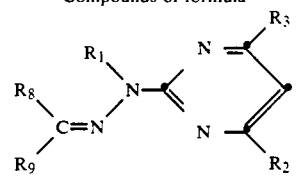

| Comp. No. | $R_1$ | $R_2$ | $R_3$ | $R_8$ | $R_9$ | physical constant |
|---|---|---|---|---|---|---|
| 3.1 | $C_6H_5$ | $CH_3$ | $CF_3$ | H | 2-CH$_3$—C$_6$H$_4$ | m.p. 188–190° C. |
| 3.2 | $C_6H_5$ | $CH_3$ | $CF_3$ | H | $C_2H_5$ | |
| 3.3 | $C_6H_5$ | $CH_3$ | $CH_3$ | H | $CH_3$ | m.p. 117–118° C. |
| 3.4 | $C_6H_5$ | $CH_3$ | cyclo-C$_3$H$_5$ | H | $CH_3$ | m.p. 137–138° C. |
| 3.5 | $C_6H_5$ | $CH_3$ | cyclo-C$_3$H$_5$ | H | $C_2H_5$ | m.p. 103–105° C. |
| 3.6 | $C_6H_5$ | $CH_3$ | $CH_3$ | H | $C_2H_5$ | m.p. 46–49° C. |
| 3.7 | $C_6H_5$ | $CH_3$ | $CH_2OCH_3$ | H | $C_2H_5$ | m.p. 51–53° C. |
| 3.8 | $C_6H_5$ | $CH_3$ | cyclo-C$_3$H$_5$ | H | n-C$_3$H$_7$ | $n_D^{25}$ 1.5862 |
| 3.9 | $C_6H_5$ | $CH_3$ | $C_2H_5$ | $CH_3$ | $CH_3$ | |
| 3.10 | 3-F—C$_6$H$_4$ | $CH_3$ | $CH_2OCH_3$ | $CH_3$ | $CH_3$ | $n_D^{24}$ 1.5678 |
| 3.11 | $C_6H_5$ | $CH_3$ | $CH_3$ | $C_2H_5$ | $CH_3$ | $n_D^{23}$ 1.5830 |
| 3.12 | 4-NO$_2$—C$_6$H$_4$ | $C_2H_5$ | $C_2H_5$ | H | n-C$_3$H$_7$ | |

TABLE 3-continued

Compounds of formula

| Comp. No. | R₁ | R₂ | R₃ | R₈ | R₉ | physical constant |
|---|---|---|---|---|---|---|
| 3.13 | $C_6H_5$ | $CH_3$ | n-$C_3H_7$ | (phenyl ring) | $CH_3$ | |
| 3.14 | $C_6H_5$ | $CH_3$ | cyclo-$C_3H_5$ | $CH_3$ | $CH_3$ | $n_D^{22}$ 1.5982 |
| 3.15 | $C_6H_5$ | $CH_3$ | cyclo-$C_3H_5$ | $CH_3$ | (cyclopentyl ring) | |
| 3.16 | $C_6H_5$ | $CH_3$ | cyclo-$C_3H_5$ | $CH_3$ | $CH_2OCH_3$ | |
| 3.17 | 4-$CF_3O$—$C_6H_4$ | $CH_3$ | cyclo-$C_3H_5$ | H | $(CH_3)_2CH$ | |
| 3.18 | 4-$CF_3O$—$C_6H_4$ | $CH_3$ | cyclo-$C_3H_5$ | H | $CH_3$ | |
| 3.19 | 3-F—$C_6H_4$ | $CH_3$ | $CH_2OCH_3$ | H | $C(CH_3)_3$ | m.p. 104–106° C. |
| 3.20 | 3-F—$C_6H_4$ | $CH_3$ | $CH_2OCH_3$ | H | $C_2H_5$ | m.p. 95–97° C. |
| 3.21 | 4-$CH_3O$—$C_6H_4$ | $CH_3$ | $CH_3$ | H | $C_2H_5$ | m.p. 81–82° C. |
| 3.22 | 4-$CH_3$—$C_6H_4$ | $(CH_3)_3C$ | $CH_3$ | H | n-$C_3H_7$ | |
| 3.23 | 4-$CH_3$—$C_6H_4$ | n-$C_3H_7$ | n-$C_3H_7$ | H | $C_2H_5$ | |
| 3.24 | $C_6H_5$ | $C_2H_5$ | $C_2H_5$ | H | $C_2H_5$ | |
| 3.25 | $C_6H_5$ | $CH_3$ | $CH_3$ | H | $(CH_3)_2CH$ | m.p. 83–84° C. |
| 3.26 | $C_6H_5$ | $CH_3$ | cyclo-$C_3H_5$ | H | $(CH_3)_2CH$ | m.p. 53–55° C. |
| 3.27 | $C_6H_5$ | $CH_3$—C≡C | cyclo-$C_3H_5$ | H | $CH_3$ | |
| 3.28 | 3F—$C_6H_4$ | $CH_3$ | cyclo-$C_3H_5$ | cyclo-$C_3H_5$ | $CH_3$ | |
| 3.29 | 4F—$C_6H_4$ | $CH_3$ | cyclo-$C_3H_5$ | $CH_3$ | $CF_3$ | |
| 3.30 | 4-$(CH_3)_2CH$—$C_6H_4$ | $CH_3$ | $CH_3$ | $C_2H_5$ | $CH_3$ | |
| 3.31 | $C_6H_5$ | $CH_3$ | $CH_3$ | —$(CH_2)_5$— | | |
| 3.32 | 2-F—$C_6H_4$ | $CH_3$ | n-$C_3H_7$ | —$(CH_2)_4$— | | |
| 3.33 | 4-I—$C_6H_4$ | $CH_3$ | $CH_3$ | $C_2H_5$ | H | |
| 3.34 | 4-I—$C_6H_4$ | cyclo-$C_3H_5$ | $CH_3$ | $(CH_3)_2CH$ | H | |
| 3.35 | $C_6H_5$ | cyclo-$C_3H_5$ | $CH_3$ | $CH_3CH=CH$— | H | m.p. 121–122° C. |
| 3.36 | $C_6H_5$ | cyclo-$C_3H_5$ | $CH_3$ | $CF_3$ | H | |
| 3.37 | $C_6H_5$ | $CH_3$ | $CH_3$ | (terpenyl group) | H | |
| 3.38 | $C_6H_5$ | $C(CH_3)_3$ | $C(CH_3)_3$ | $(CH_3)_2CH$ | H | |
| 3.39 | $C_6H_5$ | $C(CH_3)_3$ | $C(CH_3)_3$ | $C_2H_5$ | $CH_3$ | |
| 3.40 | $C_6H_5$ | $CH_3$ | cyclo-$C_3H_5$ | H | $CCl_3$ | m.p. 139–141° C. |
| 3.41 | $C_6H_5$ | $CH_3$ | $CH_3$ | $CH_2$\C(SCH_3)/$CH_2$ (cyclopropyl-SCH₃) | H | m.p. 94–96° C. |
| 3.42 | $C_6H_5$ | $CH_3$ | $CH_3$ | H | $BrCH_2$ | |
| 3.43 | $C_6H_5$ | $CH_2OCH_3$ | $CH_3$ | 2-$CH_3$—$C_6H_4$ | H | m.p. 143–145° C. |
| 3.44 | $C_6H_5$ | $CH_3$ | cyclo-$C_3H_5$ | 2-$CH_3$—$C_6H_4$ | H | m.p. 107–109° C. |
| 3.45 | $C_6H_5$ | $CH_3$ | cyclo-$C_3H_5$ | 2-F—$C_6H_4$ | $CH_3$ | |
| 3.46 | $C_6H_5$ | $CH_3$ | n-$C_5H_{11}$ | 3-$CH_3O$—$C_6H_4$ | $CH_3$ | |
| 3.47 | $C_6H_5$ | $CH_3$ | $CH_3$ | $C_6H_5$ | H | m.p. 138–140° C. |
| 3.48 | 4-$(CH_3)_2CH$—$C_6H_4$ | $CH_3$ | $CH_3$ | —$(CH_2)_3$— | | |
| 3.49 | 4-Br—$C_6H_4$ | $CH_3$ | $CH_3$ | H | (2-HO-3,5-diiodophenyl) | m.p. 255–256° C. |

TABLE 3-continued

Compounds of formula

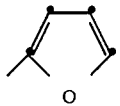

| Comp. No. | $R_1$ | $R_2$ | $R_3$ | $R_8$ | $R_9$ | physical constant |
|---|---|---|---|---|---|---|
| 3.50 | 4-F—$C_6H_4$ | cyclo-$C_3H_5$ | $CH_3$ | $CH_3$ | H | m.p. 162–164° C. |
| 3.51 | 4-F—$C_6H_4$ | cyclo-$C_3H_5$ | $CH_3$ | $CH_3$ | $CH_3$ | |
| 3.52 | 4-F—$C_6H_4$ | cyclo-$C_3H_5$ | $CH_3$ | $(CH_3)_2CH$ | H | m.p. 58–60° C. |
| 3.53 | $C_6H_5$ | $CH_3$ | $CH_3$ | H | 4-$(CH_3)_2N$—$C_6H_4$ | |
| 3.54 | $C_6H_5$ | $CH_3$ | $CH_3$ | H | 4-CN—$C_6H_4$ | |
| 3.55 | $C_6H_5$ | $CH_3$ | $CH_2OCH_3$ | H | 2-OH—$C_6H_4$ | |
| 3.56 | $C_6H_5$ | $CH_3$ | $CH_3$ | H | 2,3-$Cl_2$—$C_6H_3$ | m.p. 221–222° C. |
| 3.57 | $C_6H_5$ | $CH_3$ | $CH_3$ | H | $CH_2$=CH— | |
| 3.58 | $C_6H_5$ | $CH_3$ | $CH_3$ | —CH=CHCH$_2$CH$_2$CH$_2$— | | |
| 3.59 | $C_6H_5$ | $CH_3$ | cyclo-$C_3H_5$ | —CH=CHCH$_2$CH$_2$— | | |
| 3.60 | $C_6H_5$ | $CH_3$ | $CH_3$ | —(CH$_2$)$_4$— | | |
| 3.61 | $C_6H_5$ | $CH_3$ | cyclo-$C_3H_5$ | $CH_3$ | $CF_3$ | |
| 3.62 | $C_6H_5$ | $CH_3$ | cyclo-$C_3H_5$ | $CF_3$ | $CF_3$ | |
| 3.63 | 3,5-$(CF_3)_2$—$C_6H_3$ | $CH_3$ | $CH_3$ | $C_2H_5$ | H | $n_D^{25}$ 1.4990 |
| 3.64 | $C_6H_5$ | $CH_3$ | cyclo-$C_3H_5$ | H | $CH_2$=C(CH$_3$)— | |
| 3.65 | $C_6H_5$ | $CH_3$ | cyclo-$C_3H_5$ | H | 2-pyridyl | |
| 3.66 | $C_6H_5$ | $CH_3$ | cyclo-$C_3H_5$ | H | 3-pyridyl | |
| 3.67 | $C_6H_5$ | $CH_3$ | cyclo-$C_3H_5$ | H | 4-pyridyl | |
| 3.68 | $C_6H_5$ | $CH_3$ | $CH_2OCH_3$ | H | 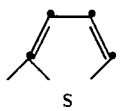 | m.p. 155–156° C. |
| 3.69 | $C_6H_5$ | $CH_3$ | $CH_3$ | H | 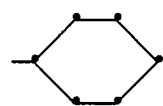 | m.p. 177–179° C. |
| 3.70 | $C_6H_5$ | $CH_3$ | cyclo-$C_3H_5$ | $CH_3SCH_2CH_2$ | H | |
| 3.71 | $C_6H_5$ | $CH_3$ | $CH_3$ | 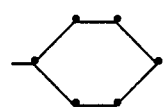 | $CH_3$ | |
| 3.72 | $C_6H_5$ | $CH_3$ | $CH_3$ | $C_6H_5$ | $CF_3$ | |
| 3.73 | $C_6H_5$ | $CH_3$ | cyclo-$C_3H_5$ | $C_6H_5$ | $CH_3$ | |
| 3.74 | $C_6H_5$ | $CH_3$ | $CH_2OCH_3$ | $CH_3$ | $CH_2N(CH_3)_2$ | |
| 3.75 | $C_6H_5$ | $CH_3$ | cyclo-$C_3H_5$ | H | $CHCl_2$ | |
| 3.76 | $C_6H_5$ | $CH_3$ | cyclo-$C_3H_5$ | H | $CBr_3$ | |
| 3.77 | $C_6H_5$ | $CH_3$ | $CH_3$ | 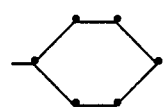 | H | |
| 3.78 | 3-F—$C_6H_4$ | $CH_3OCH_2$ | $CH_3$ | H | $(CH_3)_2CH$ | m.p. 83–84° C. |
| 3.79 | $C_6H_5$ | $CH_3OCH_2$ | $CH_3$ | H | $(CH_3)_2CH$ | $n_D^{35}$ 1.5673 |
| 3.80 | $C_6H_5$ | cyclo-$C_3H_5$ | $CH_3$ | 2,3-$Cl_2$—$C_6H_3$ | H | m.p. 179–182° C. |
| 3.81 | 4-$CF_3$—$C_6H_4$ | $CH_3$ | $CH_3$ | $CH_3$ | $CH_3$ | |
| 3.82 | 4-$CF_3$—$C_6H_4$ | $CH_3$ | $CH_3$ | H | $C_2H_5$ | |
| 3.83 | $C_6H_5$ | $CH_3$ | $CH_3$ | $CH_3(CH_2)_6$ | H | |
| 3.84 | $C_6H_5$ | $CH_3$—C≡C | cyclo-$C_3H_5$ | H | $C_2H_5$ | |
| 3.85 | 4-F—$C_6H_4$ | cyclo-$C_3H_5$ | $CH_3$ | 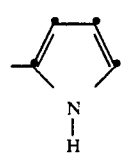 | H | m.p. 132–134° C. |

TABLE 3-continued

Compounds of formula

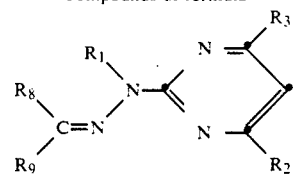

| Comp. No. | $R_1$ | $R_2$ | $R_3$ | $R_8$ | $R_9$ | physical constant |
|---|---|---|---|---|---|---|
| 3.86 | 3-F—$C_6H_4$ | cyclo-$C_3H_5$ | $CH_3$ | H | 1-methylpyrrol-2-yl | m.p. 111-112° C. |
| 3.87 | $C_6H_5$ | $CH_2OCH_3$ | $CH_3$ | $CH_3$ | H | m.p. 112-114° C. |
| 3.88 | $C_6H_5$ | $CH_3$ | $CH_3$ | cyclo-$C_3H_5$ | $CH_3$ | $n_D^{24}$ 1.600 |
| 3.89 | 3-F—$C_6H_4$ | $CH_3$ | cyclo-$C_3H_5$ | H | $CH_3$ | m.p. 114-116° C. |
| 3.90 | 3-F—$C_6H_4$ | $CH_3$ | cyclo-$C_3H_5$ | H | $C_2H_5$ | |
| 3.91 | 3-F—$C_6H_4$ | $CH_3$ | cyclo-$C_3H_5$ | H | n-$C_3H_7$ | m.p. 46-47° C. |
| 3.92 | 3-F—$C_6H_4$ | $CH_3$ | cyclo-$C_3H_5$ | H | $(CH_3)_2CH$ | m.p. 45-46° C. |
| 3.93 | $C_6H_5$ | $CH_3$ | cyclo-$C_3H_5$ | H | —CH=$CH_2$ | |
| 3.94 | 4-F—$C_6H_4$ | $CH_3$ | cyclo-$C_3H_5$ | $C_2H_5$ | H | m.p. 79-80° C. |
| 3.95 | 4-F—$C_6H_4$ | $CH_3$ | cyclo-$C_3H_5$ | n-$C_3H_7$ | H | m.p. 80-81° C. |
| 3.96 | $C_6H_5$ | $CH_3$ | cyclo-$C_3H_5$ | H | $C(CH_3)_2CH_2SCH_3$ | |
| 3.97 | $C_6H_5$ | $CH_3$ | cyclo-$C_3H_5$ | $C_2H_5$ | $CH_3$ | |
| 3.98 | 3-F—$C_6H_4$ | $CH_3$ | cyclo-$C_3H_5$ | $CH_3$ | $CH_3$ | |
| 3.99 | 3-F—$C_6H_4$ | $CH_3$ | cyclo-$C_3H_5$ | $CH_3$ | $C_2H_5$ | |
| 3.100 | 3-F—$C_6H_4$ | $CH_3$ | cyclo-$C_3H_5$ | $CH_3$ | $CF_3$ | |
| 3.101 | 3-F—$C_6H_4$ | $CH_3$ | cyclo-$C_3H_5$ | $CCl_3$ | H | |
| 3.102 | 3-F—$C_6H_4$ | $CH_3$ | cyclo-$C_3H_5$ | $CH_2OCH_3$ | $CH_3$ | |
| 3.103 | $C_6H_5$ | $CH_2OCH_3$ | cyclo-$C_3H_5$ | H | 1-naphthyl | m.p. 127-128° C. |
| 3.104 | 3-F-$C_6H_4$ | $CH_2OCH_3$ | $CH_3$ | H | 2-pyridyl | |
| 3.105 | 3-F-$C_6H_4$ | cyclo-$C_3H_5$ | $CH_3$ | $CH_3SCH_2CH_2$ | H | |
| 3.106 | 3-F-$C_6H_4$ | cyclo-$C_3H_5$ | $CH_3$ | $(CH_3)_3C$ | H | m.p. 104-105° C. |
| 3.107 | $C_6H_5$ | cyclo-$C_3H_5$ | $CH_3$ | $(CH_3)_3C$ | H | m.p. 100-102° C. |
| 3.108 | $C_6H_5$ | cyclo-$C_3H_5$ | $CH_3$ | H | 2-methylthien-5-yl | m.p. 90-92° C. |
| 3.109 | $C_6H_5$ | cyclo-$C_3H_5$ | $CH_3$ | H | cyclo-$C_3H_5$ | |
| 3.110 | $C_6H_5$ | $CH_3$ | $CH_3$ | 2-pyridyl | $CH_3$ | |
| 3.111 | $C_6H_5$ | $CH_3$ | $CH_3$ | $CH_3$ | 2,4-$Cl_2$—$C_6H_3$ | |
| 3.112 | $C_6H_5$ | $CH_3$ | $CH_3$ | $CH_3$ | $(CH_2)_7CH_3$ | |
| 3.113 | 3-F—$C_6H_4$ | $CH_3$ | $CH_2OCH_3$ | 4-pyridyl | H | m.p. 190-192° C. |
| 3.114 | $C_6H_5$ | $CH_3$ | $CH_2OCH_3$ | H | 2,3-$Cl_2$—$C_6H_3$ | m.p. 185-186° C. |
| 3.115 | $C_6H_5$ | $CH_3$ | $CH_2OCH_3$ | 1-methylpyrrol-2-yl | H | m.p. 121-122° C. |
| 3.116 | 3-F—$C_6H_4$ | $CH_3$ | $CH_2OCH_3$ | $CH_3$ | H | m.p. 144-145° C. |
| 3.117 | $C_6H_5$ | $CH_3$ | $CH_2OCH_3$ | H | n-$C_3H_7$ | $n_D^{25}$ 1.5756 |
| 3.118 | $C_6H_5$ | $CH_3$ | $CH_3$ | H | $C(CH_3)_3$ | m.p. 73-74° C. |
| 3.119 | $C_6H_5$ | $CH_3$ | $CH_2OCH_3$ | H | $C(CH_3)_3$ | m.p. 100-101° C. |
| 3.120 | $C_6H_5$ | $CH_3$ | $CH_3$ | H | n-$C_3H_7$ | $n_D^{25}$ 1.5860 |
| 3.121 | 3-F—$C_6H_4$ | $CH_3$ | $CH_2OCH_3$ | H | n-$C_3H_7$ | m.p. 47-48° C. |

TABLE 3-continued

Compounds of formula $$\begin{array}{c} R_8 \\ \diagdown \\ R_9 \end{array} C=N-N \begin{array}{c} R_1 \\ \diagdown \\ \end{array} \begin{array}{c} N= \\ \diagdown \\ N \end{array} \begin{array}{c} R_3 \\ \diagdown \\ R_2 \end{array}$$

| Comp. No. | $R_1$ | $R_2$ | $R_3$ | $R_8$ | $R_9$ | physical constant |
|---|---|---|---|---|---|---|
| 3.122 | 4-F—$C_6H_4$ | $CH_3$ | cyclo-$C_3H_5$ | H | $C(CH_3)_3$ | m.p. 27–128° C. |

TABLE 4

Compounds of formula $$R_{10}R_{(11)}N-N\begin{array}{c} R_1 \\ \diagdown \\ \end{array} \begin{array}{c} N= \\ \diagdown \\ N \end{array} \begin{array}{c} R_3 \\ \diagdown \\ R_2 \end{array}$$

| Comp. | $R_1$ | $R_2$ | $R_3$ | $R_{10}$ | $R_{11}$ | physical constant |
|---|---|---|---|---|---|---|
| 4.1 | $C_6H_5$ | $CH_3$ | $CH_3$ | H | $CH_3$ | $n_D^{25}$ 1.5963 |
| 4.2 | $C_6H_5$ | $CH_3$ | $CH_3$ | H | $C_2H_5$ | |
| 4.3 | $C_6H_5$ | $CH_3$ | $CH_3$ | H | $CH_2CH=CH_2$ | |
| 4.4 | $C_6H_5$ | $CH_3$ | $CH_3$ | H | n-$C_3H_7$ | $n_D^{24}$ 1.5740 |
| 4.5 | $C_6H_5$ | cyclo-$C_3H_5$ | $CH_3$ | H | $CH_2C\equiv CH$ | |
| 4.6 | 4-$CH_3O$—$C_6H_4$ | $CH_3$ | $CH_3$ | H | n-$C_5H_{11}$ | |
| 4.7 | $C_6H_5$ | $CH_3$ | cyclo-$C_3H_5$ | (2-thienyl)-$CH_2$— | H | $n_D^{25}$ 1.6160 |
| 4.8 | 3,4-$(CH_3)_2$—$C_6H_3$ | $CH_3$ | $CH_3$ | (2-thienyl)-$CH_2$— | H | |
| 4.9 | 4-$CF_3$—$C_6H_4$ | $CH_3$ | $CH_3$ | (2-thienyl)-$CH_2$— | $CH_3$ | |
| 4.10 | 3-F—$C_6H_4$ | $CH_3$ | cyclo-$C_3H_5$ | n-$C_3H_7$ | n-$C_3H_7$ | $n_D^{27}$ 1.5510 |
| 4.11 | $C_6H_5$ | $CH_2OCH_3$ | $CH_3$ | $CH_2C(CH_3)_3$ | H | |
| 4.12 | $C_6H_5$ | $CH_2OCH_3$ | $CH_3$ | (2-pyridyl)-$CH_2$— | H | |
| 4.13 | $C_6H_5$ | $CH_3$ | $CH_3$ | $CH_3$ | $CH_3$ | $n_D^{25}$ 1.5673 |
| 4.14 | $C_6H_5$ | $CH_3$ | $CH_3$ | $C_6H_5CH_2$— | H | m.p. 56–47° C. |
| 4.15 | $C_6H_5$ | $CH_3$ | cyclo-$C_3H_5$ | (2-pyrrolyl)-$CH_2$— | H | |

TABLE 4-continued

Compounds of formula

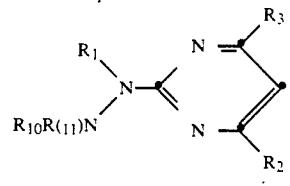

| Comp. | R₁ | R₂ | R₃ | R₁₀ | R₁₁ | physical constant |
|---|---|---|---|---|---|---|
| 4.16 | 4-F—$C_6H_4$ | $CH_3$ | cyclo-$C_3H_5$ | (2-aminomethyl-dihydropyridinyl) | H | m.p. 83-84° C. |
| 4.17 | $C_6H_5$ | $CH_2OCH_3$ | $CH_3$ | H | $CH_3$ | $n_D^{24}$ 1.5793 |
| 4.18 | $C_6H_5$ | $CH_2OCH_3$ | $CH_3$ | $CH_3CH=CHCH_2$— | H | |
| 4.19 | $C_6H_5$ | $CH_2OCH_3$ | $CH_3$ | $CF_3CH_2$ | H | |
| 4.20 | $C_6H_5$ | $CH_2OCH_3$ | $CH_3$ | n-$C_3H_7$ | H | $n_D^{25}$ 1.5635 |
| 4.21 | $C_6H_5$ | $CH_2OCH_3$ | $CH_3$ | 2-hydroxybenzyl | H | |
| 4.22 | 4-F—$C_6H_4$ | $CH_3$ | cyclo-$C_3H_5$ | $C_2H_5$ | H | $n_D^{23}$ 1.5693 |
| 4.23 | 3-Br—$C_6H_4$ | $CH_3$ | cyclo-$C_3H_5$ | n-$C_4H_9$ | $CH_3$ | |
| 4.24 | 2-Cl-4-$CF_3$—$C_6H_3$ | $CH_3$ | $CH_3$ | $CH_3$ | $C_2H_5$ | |
| 4.25 | $C_6H_5$ | $C_2H_5$ | $CH_3$ | H | $CH_3$ | |
| 4.26 | $C_6H_5$ | n-$C_3H_5$ | $CH_3$ | H | $CH_3$ | |
| 4.27 | $C_6H_5$ | $CH(CH_3)_2$ | $CH(CH_3)_2$ | H | $CH_3$ | |
| 4.28 | $C_6H_5$ | $CH_3$ | $C(CH_3)_3$ | H | $CH_3$ | |
| 4.29 | $C_6H_5$ | $C_2H_5$ | $C_2H_5$ | H | $CH_3$ | |
| 4.30 | $C_6H_5$ | $CH_3$ | $CH_2OCH_3$ | H | furfuryl | |
| 4.31 | 4-F—$C_6H_4$ | $CH_3$ | $CH_3$ | $C_2H_5$ | $C_2H_5$ | $n_D^{25}$ 1.5533 |
| 4.32 | 4-F—$C_6H_4$ | $CH_3$ | $CH_3$ | $CH_3$ | H | m.p. 57-59° C. |
| 4.33 | $C_6H_5$ | $CH_3$ | $CH_3$ | $CH_2CCl_3$ | H | |
| 4.34 | $C_6H_5$ | $CH_3$ | $CH_3$ | 1-(2-pyridyl)ethyl | H | |
| 4.35 | $C_6H_5$ | $CH_3$ | $CH_3$ | $(CH_3)_2CH$ | H | |
| 4.36 | $C_6H_5$ | cyclo-$C_3H_5$ | $CH_3$ | $(CH_3)_2CH$ | H | $n_D^{24}$ 1.5772 |
| 4.37 | $C_6H_5$ | cyclo-$C_3H_5$ | $CH_3$ | $C_2H_5(CH_3)CH$— | H | |
| 4.38 | $C_6H_5$ | $CH_3$ | $CH_3$ | $Br_3CCH_2$— | H | |
| 4.39 | $C_6H_5$ | $CH_3$ | $CH_3$ | $CH_2CH_2CN$ | H | |
| 4.40 | $C_6H_5$ | $CH_3$ | $CH_3$ | $CH_2CH_2CN$ | $CH_2CH_2CN$ | |
| 4.41 | $C_6H_5$ | $CH_3$ | cyclo-$C_3H_5$ | $CH_2CH_2CN$ | $CH_2CH_2CN$ | |
| 4.42 | $C_6H_5$ | $CH_3$ | cyclo-$C_3H_5$ | $CH_2CH_2CN$ | H | |
| 4.43 | $C_6H_5$ | $CH_3$ | cyclo-$C_3H_5$ | cyclo-$C_6H_{11}$ | H | m.p. 75-77° C. |
| 4.44 | $C_6H_5$ | $CH_3$ | cyclo-$C_3H_5$ | $C_2H_5$ | H | $n_D^{25}$ 1.5830 |
| 4.45 | $C_6H_5$ | $CH_3$ | cyclo-$C_3H_5$ | $CH_3$ | H | $n_D^{29}$ 1.5983 |
| 4.46 | 3-F—$C_6H_4$ | $CH_3$ | cyclo-$C_3H_5$ | $CH_3$ | H | $n_D^{36}$ 1.5842 |
| 4.47 | 3-F—$C_6H_4$ | $CH_3$ | cyclo-$C_3H_5$ | $C_2H_5$ | H | $n_D^{23}$ 1.5778 |
| 4.48 | 4-F—$C_6H_4$ | $CH_3$ | cyclo-$C_3H_5$ | $C_2H_5(CH_3)CH$ | H | |
| 4.49 | $C_6H_5$ | $CH_3$ | $CH_3$ | H | cyclo-C-$C_6H_{11}$ | |
| 4.50 | $C_6H_5$ | $CH_3$ | $CH_3$ | H | cyclo-$C_6H_{11}$ | |
| 4.51 | $C_6H_5$ | $CH_3$ | $CH_3$ | H | cyclo-$C_5H_9$ | m.p. 84-86° C. |

TABLE 4-continued

Compounds of formula

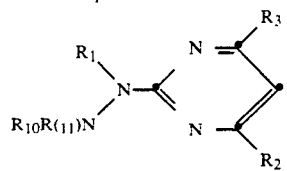

| Comp. | $R_1$ | $R_2$ | $R_3$ | $R_{10}$ | $R_{11}$ | physical constant |
|---|---|---|---|---|---|---|
| 4.52 | $C_6H_5$ | $CH_2OCH_3$ | $CH_3$ | $CH_3OCH_2(CH_3)CH-$ | H | $n_D^{24}$ 1.5565 |
| 4.53 | $C_6H_5$ | $CH_2OCH_3$ | $CH_3$ | $(CH_3)_2NCH_2(CH_3)CH-$ | H | |
| 4.54 | 3-F—$C_6H_4$ | $CH_2OCH_3$ | $CH_3$ | H | $(CH_3)CHCH_2$ | |
| 4.55 | 3-F—$C_6H_4$ | $CH_2OCH_3$ | $CH_3$ | H | $n$-$C_3H_7$ | |
| 4.56 | 3-F—$C_6H_4$ | $CH_2OCH_3$ | $CH_3$ | $(CH_3)_2CH$ | H | $n_D^{23}$ 1.5450 |
| 4.57 | 4-I—$C_6H_4$ | $CH_3$ | $CH_3$ | NC—C6H4—$CH_2$ | H | |
| 4.58 | $C_6H_5$ | $CH_3$ | cyclo-$C_3H_5$ | H | cyclo-$C_6H_{11}$ | m.p. 75–77° C. |
| 4.59 | $C_6H_5$ | $CH_3$ | cyclo-$C_3H_5$ | cyclo-$C_3H_5$-CH(CH$_3$)— | H | |
| 4.60 | $C_6H_5$ | $CH_3$ | cyclo-$C_3H_5$ | H | $n$-$C_3H_7$ | |
| 4.61 | $C_6H_5$ | $CH_3$ | cyclo-$C_3H_5$ | H | $C_6H_5$ | m.p. 125–127° C. |
| 4.62 | $C_6H_5$ | $CH_3$ | cyclo-$C_3H_5$ | $CF_3CH_2$ | H | |
| 4.63 | 2-F—$C_6H_4$ | $CH_3$ | cyclo-$C_3H_5$ | $Br_3CCH_2$ | H | |
| 4.64 | 2-F—$C_6H_4$ | $C_2H_5$ | $CH_3$ | $Cl_2CHCH_2$ | H | |
| 4.65 | 4-F—$C_6H_4$ | $CH_3$ | cyclo-$C_3H_5$ | $CH_3(F_3C)CH$ | H | |
| 4.66 | 4-F—$C_6H_4$ | $CH_3$ | cyclo-$C_3H_5$ | H | cyclo-$C_3H_5$-CH(CH$_3$)— | |
| 4.67 | 4-F—$C_6H_4$ | $CH_3$ | cyclo-$C_3H_5$ | H | $n$-$C_3H_7$ | |
| 4.68 | 4-F—$C_6H_4$ | $CH_3$ | cyclo-$C_3H_5$ | H | $(CH_3)_2CHCH_2$ | |
| 4.69 | $C_6H_5$ | $CH_3$ | $CH_2OCH_3$ | $CH_3$ | $CH_3$ | $n_D^{24}$ 1.5595 |
| 4.70 | $C_6H_5$ | $CH_3$ | $CH_2OCH_3$ | $n$-$C_3H_7$ | $n$-$C_3H_7$ | $n_D^{23}$ 1.5483 |
| 4.71 | $C_6H_5$ | $CH_3$ | $CH_2OCH_3$ | H | $CH_3(CH)_7$ | |
| 4.72 | $C_6H_5$ | $CH_3$ | $CH_2OCH_3$ | $BrCH_2CHO$ | H | |
| 4.73 | $C_6H_5$ | $CH_3$ | $CH_2OCH_3$ | N-methylpyrrolyl-$CH_2-$ | H | m.p. 67–68° C. |
| 4.74 | $C_6H_5$ | $CH_3$ | $CH_3$ | H | $C_2H_5(CH_3)CH-$ | $n_D^{23}$ 1.5638 |
| 4.75 | $C_6H_5$ | $CH_3$ | $CH_3$ | $C_6H_5(CF_3)CH-$ | H | |
| 4.76 | $C_6H_5$ | $CH_3$ | $CH_3$ | H | (SCH$_3$)cyclopropyl-$CH_2-$ | |
| 4.77 | $C_6H_5$ | $CH_3$ | $CH_3$ | $(CH_3)_2CHCH_2$ | H | $n_D^{24}$ 1.5623 |

TABLE 4-continued

Compounds of formula

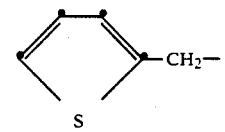

| Comp. | R₁ | R₂ | R₃ | R₁₀ | R₁₁ | physical constant |
|---|---|---|---|---|---|---|
| 4.78 | $C_6H_5$ | $CH_3$ | $CH_3$ | H | 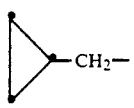 | $n_D^{25}$ 1.6175 |
| 4.79 | $C_6H_5$ | $CH_3$ | $CH_3$ | 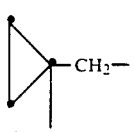 | H | |
| 4.80 | $C_6H_5$ | $CH_3$ | $CH_3$ | $CF_3CH_2-$ | H | |
| 4.81 | $C_6H_5$ | $CH_3$ | cyclo-$C_3H_5$ | $CH_3$ | $C_2H_5$ | $n_D^{24}$ 1.5803 |
| 4.82 | $C_6H_5$ | $CH_3$ | cyclo-$C_3H_5$ | H | $Br_3CCH_2-$ | |
| 4.83 | $C_6H_5$ | $CH_3$ | cyclo-$C_3H_5$ | 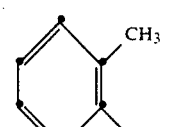 | H | |
| 4.84 | $C_6H_5$ | $CH_3$ | cyclo-$C_3H_5$ | H | 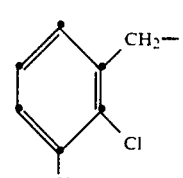 | m.p. 62-63° C. |
| 4.85 | $C_6H_5$ | $CH_3$ | cyclo-$C_3H_5$ | H |  | m.p. 67-68° C. |
| 4.86 | $C_6H_5$ | $CH_3$ | cyclo-$C_3H_5$ |  | H | |
| 4.87 | $C_6H_5$ | $CH_3$ | cyclo-$C_3H_5$ | H | $(CH_3)_2CHCH_2-$ | $n_D^{25}$ 1.5733 |
| 4.88 | $C_6H_5$ | $CH_3$ | cyclo-$C_3H_5$ | H | $CH_3CH=CHCH_2-$ | |
| 4.89 | $C_6H_5$ | $CH_3$ | cyclo-$C_3H_5$ | $C_6H_5CH_2$ | H | |
| 4.90 | 4-F—$C_6H_4$ | $CH_3$ | cyclo-$C_3H_7$ | n-$C_3H_7$ | n-$C_3H_7$ | $n_D^{23}$ 1.5483 |
| 4.91 | 3-F—$C_6H_4$ | $CH_3OCH_2$ | $CH_3$ | H | $CH_3$ | |
| 4.92 | 3-F—$C_6H_4$ | $CH_3OCH_2$ | $CH_3$ | H | $C_2H_5$ | |
| 4.93 | 3-F—$C_6H_4$ | $CH_3OCH_2$ | $CH_3$ | H | n-$C_4H_9$ | |
| 4.94 | 4-$CF_3O$—$C_6H_4$ | $CH_3OCH_2$ | $CH_3$ | H | $C_2H_5$ | |
| 4.95 | 4-$CF_3O$—$C_6H_4$ | $CH_3OCH_2$ | $CH_3$ | $CH_3$ | $CH_3$ | |
| 4.96 | 4-I—$C_6H_4$ | $CH_3$ | cyclo-$C_3H_5$ | H | n-$C_3H_7$ | |
| 4.97 | 4-I—$C_6H_4$ | $CH_3$ | cyclo-$C_3H_5$ | H | $(CH_3)_2CHCH_2$ | |
| 4.98 | $C_6H_5$ | $CH_3$ | cyclo-$C_3H_5$ | $CH_3$ | $CH_3$ | $n_D^{31}$ 1.5813 |
| 4.99 | $C_6H_5$ | $CH_3$ | cyclo-$C_3H_5$ | $C_2H_5$ | $C_2H_5$ | $n_D^{24}$ 1.5762 |
| 4.100 | $C_6H_5$ | $CH_3$ | cyclo-$C_3H_5$ | H | $CH_2=CHCH_2-$ | |
| 4.101 | $C_6H_5$ | $CH_3$ | cyclo-$C_3H_5$ | $CH_3SCH_2CH_2CH_2$ | H | |
| 4.102 | $C_6H_5$ | $CH_3$ | cyclo-$C_3H_5$ | $CH_3$ | $CH_2CH(CH_3)_2$ | $n_D^{30}$ 1.5613 |
| 4.103 | $C_6H_5$ | $CH_3$ | cyclo-$C_3H_5$ |  | H | |

TABLE 4-continued

Compounds of formula $$R_1\text{-N}(R_{10}R_{(11)}N)\text{-C}=N-... $$

| Comp. | $R_1$ | $R_2$ | $R_3$ | $R_{10}$ | $R_{11}$ | physical constant |
|---|---|---|---|---|---|---|
| 4.104 | $C_6H_5$ | $C_2H_5$ | $CH_2OCH_3$ | H | $CH_3$ | $n_D^{24}$ 1.5753 |
| 4.105 | $C_6H_5$ | $CH_3$ | $CH_3$ | $CH_2=C(CH_3)-CH_2-$ | H | |
| 4.106 | $C_6H_5$ | cyclo-$C_3H_5$ | $CH_3$ | $CH_3OCH_2(CH_3)CH-$ | $CH_3$ | |
| 4.107 | $C_6H_5$ | cyclo-$C_3H_5$ | $CH_3$ | $CF_3(CH_3)CH-$ | $CH_3$ | |
| 4.108 | $C_6H_5$ | cyclo-$C_3H_5$ | $CH_3$ | $(CF_3)_2CH-$ | H | |
| 4.109 | 3-F—$C_6H_4$ | n-$C_3H_7$ | n-$C_3H_7$ | H | n-$C_3H_7$ | |
| 4.110 | 3-F—$C_6H_4$ | $CH_3$ | cyclopropyl | $CH_3$ | $CH_3$ | $n_D^{23}$ 1.5765 |
| 4.111 | $C_6H_5$ | $CH_3$ | cyclopropyl | $CH_2C(CH_3)_3$ | H | m.p. 69–70° C. |

2. Formulation Example for liquid active ingredients of formula I (throughout, percentages are by weight)

| 2.1. Emulsifiable concentrates | a) | b) | c) |
|---|---|---|---|
| a compound of Table 1 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 2.2. Solutions | a) | b) | c) | d) |
|---|---|---|---|---|
| a compound of Table 1 | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 160–190° C.) | — | — | 94% | — |

These solutions are suitable for application in the form of micro-drops.

| 2.3. Granulates | a) | b) |
|---|---|---|
| a compound of Table 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4. Dusts | a) | b) |
|---|---|---|
| a compound of Table 1 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Formulation Examples for solid active ingredients of formula I (throughout, percentages are by weight)

| 2.5. Wettable powders | a) | b) | c) |
|---|---|---|---|
| a compound of Table 1 | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2.6. Emulsifiable concentrate | |
|---|---|
| a compound of Table 1 | 10% |
| octylphenol polyethylene glycol | 3% |

| 2.6. Emulsifiable concentrate | |
|---|---|
| ether (4-5 moles of ethylene oxide) calcium dodecylbenzenesulfonate | 3% |
| castor oil polyglycol ether (35 moles of ethylene oxide) | 4% |
| cyclohexanone | 34% |
| xylene mixture | 50% |

Emulsions of any required concentration can be obtained from this concentrate by dilution with water.

| 2.7. Dusts | a) | b) |
|---|---|---|
| a compound of Table 1 | 5% | 8% |
| talcum | 95% | — |
| kaolin | — | 92% |

Ready-for-use dusts are obtained by mixing the active ingredient with the carrier and grinding the mixture in a suitable mill.

| 2.8. Extruder granulate | |
|---|---|
| a compound of Table 1 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.9. Coated granulate | |
|---|---|
| a compound of Table 1 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| 2.10. Suspension concentrate | |
|---|---|
| a compound of Table 1 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

3. Biological Examples

Example 3.1

Action against *Venturia inaequalis* on apple shoots

Residual protective action

Apple cuttings with 10-20 cm long fresh shoots are sprayed with a spray mixture (0.006% active ingredient) prepared from a wettable powder formulation of the test compound. The treated plants are infected 24 hours later with a conidia suspension of the fungus. The plants are then incubated for 5 days at 90-100% relative humidity and stood in a greenhouse for a further 10 days at 20°-24° C. Scab infestation is evaluated 15 days after infection.

Compounds of the Tables exhibit good activity against Venturia (infestation: less than 20%). For example, compounds 1.79, 1.108, 1.122 and 4.45 reduce Venturia infestation to 0 to 10%. On the other hand, Venturia infestation is 100% on untreated and infected control plants.

Example 3.2

Action against *Botrytis cinerea* on apples

Residual protective action

Artificially damaged apples are treated by dripping onto the damaged areas a spray mixture (0.002% or 0.02% active ingredient) prepared from a wettable powder formulation or an emulsifiable concentrate of the rest compound. The treated fruits are then inoculated with a spore suspension of the fungus and incubated for one week at high humidity and about 20° C. Evaluation of the fungicidal action of the test compound is made by counting the number of damaged areas that have rotted.

Compounds of the Tables exhibit good activity against Botrytis (attack: less than 20%). For example, compounds 1.4, 1.6, 1.7, 1.12, 1.17, 1.48, 1.55, 1.56, 1.65, 1.68, 1.79, 1.104, 1.108, 1.118, 1.119, 1.122, 1.124, 1.129, 1.137, 1.138, 3.5, 3.6, 3.7, 3.8, 3.10, 3.11, 3.25, 3.26, 3.35, 3.40, 3.41, 3.50, 3.52, 3.78, 3.79, 3.113, 3.115, 4.1, 4.4, 4.15, 4.17, 4.20, 4.45, 4.56, 4.73, 4.74, 4.87 and 4.98 reduce Botrytis attack to 0 to 10%. On the other hand, Botrytis attack is 100% on untreated and infected control plants.

Example 3.3

Action against *Erysiphe graminis* in barley a) Residual protective action

Barley plants about 8 cm in height are sprayed with a spray mixture (0.02% active ingredient) prepared from a wettable powder formulation of the test compound. The treated plants are dusted with conidia of the fungus after 3 to 4 hours. The infected barley plants are stood in a greenhouse at about 22° C. and the fungus attack is evaluated after 10 days.

Compounds of the Tables exhibit good activity against Erysiphe (attack: less than 20%). For example, compounds 1.32, 1.56, 1.104, 1.122, 1.124, 3.5, 3.8, 3.44 and 3.52 reduce the Erysiphe attack to 0 to 10%. On the other hand, Erysiphe attack is 100% on untreated and infected control plants.

Example 3.4

Action against *Helminthosporium gramineum*

Wheat grains are contaminated with a spore suspension of the fungus and dried. The contaminated grains are dressed with a suspension of the test compound prepared from a wettable powder (600 ppm of active ingredient based on the weight of the seeds). Two days later the grains are placed in suitable agar dishes and after a further 4 days the development of the fungus colonies around the grains is evaluated. Evaluation of the test compound is made according to the number and size of the fungus colonies. Compounds of the Tables inhibit fungus attack substantially (less than 20% fungus attack).

Example 3.5

Action against *Colletotrichum lagenarium* on cucumbers

Cucumber plants are grown for 2 weeks and are then sprayed with a spray mixture (concentration 0.002%) prepared from a wettable powder formulation of the test compound. 2 days later, the plants are infected with a spore suspension ($1.5 \times 10^5$ spores/ml) of the fungus and incubated for 36 hours at 23° C. and high humidity. Incubation is then continued at normal humidity and approximately 22°-23° C. The fungus attack which occurs is evaluated 8 days after infection. Fungus attack is 100% on untreated and infected control plants.

Compounds of the Tables exhibit good activity and prevent the disease from spreading. Fungus attack is reduced to 20% or less.

Example 3.6

Action against *Puccinia graminis* in wheat

Wheat plants are sprayed 6 days after sowing with a spray mixture (0.02% active ingredient) prepared from a wettable powder formulation of the test compound. After 24 hours the treated plants are infected with a uredospore suspension of the fungus. The infected plants are incubated for 48 hours at 95-100% relative humidity and about 20° C. and then stood in a greenhouse at about 22° C. Evaluation of rust pustule development is made 12 days after infection.

Compounds of the Tables exhibit good activity against Puccinia (attack: less than 20%). For example, compound no. 3.10 reduces Puccinia attack to 0 to 10%. On the other hand, Puccinia attack is 100% on untreated and infected control plants.

Example 3.7

Action against Phytophthora on tomato plants a) Residual protective action

After a cultivation period of 3 weeks, tomato plants are sprayed with a spray mixture (0.02% active ingredient) prepared from a wettable powder formulation of the test compound. The treated plants are infected 24 hours later with a sporangia suspension of the fungus. Evaluation of the fungus attack is made after the infected plants have been incubated for 5 days at 90-100% relative humidity and 20° C.

b) Systemic action

After a cultivation period of 3 weeks, tomato plants are watered with a spray mixture (0.002% active ingredient based on the volume of the soil) prepared from a wettable powder formulation of the test compound. Care is taken that the spray mixture does not come into contact with the parts of the plants above the soil. The treated plants are infected 48 hours later with a sporangia suspension of the fungus. Evaluation of the fungus attack is made after the infected plants have been incubated for 5 days at 90-100% relative humidity and 20° C.

Compounds of the Tables exhibit good activity against Phytophthora (attack: less than 20%). For example, compounds 1.104, 1.122, 4.31 and 4.98 reduce Phytophthora attack to 0 to 10%. On the other hand, Phytophthora attack is 100% on untreated and infected control plants.

What is claimed is:

1. A compound of formula I

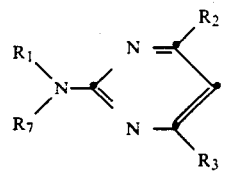

wherein: $R_1$ is phenyl or phenyl mono- to tri-substituted by $R_4$; $R_2$ is hydrogen, $C_1$-$C_5$alkyl, $C_1$-$C_5$alkyl substituted by the radical $OR_5$ or by the radical $SR_5$, $C_3$-$C_6$-cycloalkyl, $C_3$-$C_6$cycloalkyl mono- to tri-substituted by $C_1$-$C_4$alkyl or by halogen, $C_2$-$C_5$alkenyl, $C_2$-$C_5$alkynyl or the formyl radical; $R_3$ is hydrogen, $C_1$-$C_4$alkyl, $C_1$-$C_4$alkyl substituted by halogen, cyano or by the radical $OR_5$ or by the radical $SR_5$, $C_3$-$C_6$cycloalkyl or $C_3$-$C_6$cycloalkyl mono- to tri-substituted by $C_1$-$C_4$alkyl or by halogen; $R_4$ is halogen, $C_1$-$C_3$alkyl, $C_1$-$C_2$haloalkyl, $C_1$-$C_3$alkoxy or $C_1$-$C_3$haloalkoxy; $R_5$ is hydrogen, $C_1$-$C_5$alkyl, $C_3$-$C_5$alkenyl, $C_3$-$C_5$alkynyl or the radical $(CH_2)_n$—X—$C_1$-$C_3$-alkyl;

$R_7$ is the group —$NH_2$,

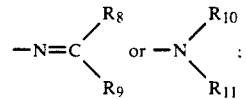

$R_8$ is hydrogen, $C_1$-$C_3$alkyl or $C_1$-$C_3$haloalkyl; $R_9$ is hydrogen, $C_1$-$C_8$alkyl, $C_1$-$C_3$alkyl substituted by hydroxy, $OR_{12}$, $SR_{12}$ or by $N(R_{12})_2$, $C_3$-$C_6$cycloalkyl, cyclopropyl substituted by $SR_{12}$, $C_3$-$C_{10}$alkenyl, $C_1$-$C_3$haloalkyl, phenyl, phenyl mono- to tri-substituted by halogen, $C_1$-$C_3$alkyl, $C_1$-$C_3$alkoxy, $C_1$-$C_3$haloalkoxy, $C_1$-$C_2$haloalkyl, hydroxy, nitro, cyano, amino or by dimethylamino, 1- or 2-naphthyl, 1-, 2- or 3-pyridyl,

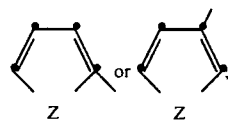

$R_8$ and $R_9$, together with the carbon atom in the radical $R_7$, are a saturated or unsaturated ring comprising 4 to 7 carbon atoms; $R_{10}$ is $CH(R_8)R_9$, phenyl, $C_3$-$C_5$alkenyl, $C_3$-$C_5$alkynyl or cyanoalkyl having 2 or 3 carbon atoms in the alkyl radical; $R_{11}$ is hydrogen, $C_1$-$C_5$alkyl, $C_3$-$C_5$alkenyl, $C_3$-$C_5$alkynyl or cyanoalkyl having 2 or 3 carbon atoms in the alkyl radical; $R_{12}$ is $CH_3$ or $C_2H_5$; X is oxygen or sulfur; Z is O, S, NH or $NCH_3$; and n is 1 to 3; including the acid addition salts and metal salt complexes thereof.

2. A compound of formula I according to claim 1, wherein: $R_1$ is phenyl or phenyl mono- to tri-substituted by $R_4$; $R_2$ is hydrogen, $C_1$-$C_5$alkyl, $C_1$-$C_5$alkyl substituted by the radical $OR_5$ or by the radical $SR_5$, $C_3$-$C_6$-cycloalkyl, $C_3$-$C_6$cycloalkyl mono- to tri-substituted by $C_1$-$C_4$alkyl or by halogen, $C_2$-$C_5$alkenyl, $C_2$-$C_5$alkynyl or the formyl radical; $R_3$ is $C_1$-$C_4$alkyl, $C_1$-$C_4$alkyl substituted by halogen, cyano or by the radical $OR_5$ or by the radical $SR_5$, $C_3$-$C_6$cycloalkyl or $C_3$-$C_6$cycloalkyl mono- to tri-substituted by $C_1$-$C_4$alkyl or by halogen; $R_4$ is halogen or $C_1$-$C_3$alkyl; $R_5$ is hydrogen, $C_1$-$C_5$alkyl, $C_3$-$C_5$alkenyl, $C_3$-$C_5$alkynyl or the radical $(CH_2)_n$—X—$C_1$-$C_3$alkyl; $R_9$ is hydrogen, $C_1$-$C_5$alkyl, $C_3$-$C_6$cycloalkyl, $C_3$-$C_5$alkenyl, $C_1$-$C_3$haloalkyl, phenyl or phenyl mono- to tri-substituted by halogen, methyl, methoxy, halomethoxy or by halomethyl; $R_8$ and $R_9$, together with the carbon atom in the radical $R_7$, are a saturated or unsaturated ring comprising 5 or 6 carbon atoms; $R_7$, $R_{10}$, $R_{11}$, $R_{12}$ and Z are as defined under formula I; X is oxygen or sulfur; and n is 1 to 3.

3. A compound of formula I according to claim 1, wherein: $R_1$ is phenyl or phenyl mono-substituted by halogen; $R_2$ is hydrogen, $C_1$-$C_5$alkyl, $C_1$-$C_5$alkyl substituted by $OR_5$, $C_3$-$C_6$cycloalkyl, $C_3$-$C_6$cycloalkyl mono- to tri-substituted by $C_1$-$C_4$alkyl or by halogen, $C_2$-$C_5$alkenyl, $C_2$-$C_5$alkynyl or the formyl radical; $R_3$ is $C_1$-$C_4$alkyl, $C_1$-$C_4$alkyl substituted by halogen, cyano or by $OR_5$, $C_3$-$C_6$cycloalkyl or $C_3$-$C_6$cycloalkyl substituted by methyl; $R_5$ is hydrogen or $C_1$-$C_2$alkyl; $R_9$ is hydrogen, $C_1$-$C_5$alkyl, $C_3$-$C_6$cycloalkyl, $C_3$-$C_5$alkenyl, $C_1$-$C_3$haloalkyl, phenyl or phenyl mono- to tri-substituted by halogen, methyl, methoxy, halomethoxy or by halomethyl; $R_8$ and $R_9$, together with the carbon atom in the radical $R_7$, are a saturated or unsaturated ring comprising 5 or 6 carbon atoms; and $R_7$, $R_{10}$, $R_{11}$ and $R_{12}$ are as defined under formula I.

4. A compound of formula I according to claim 1, wherein: $R_1$ is phenyl or phenyl mono- to tri-substituted by $R_4$; $R_2$ is hydrogen, $C_1$-$C_5$alkyl, $C_1$-$C_5$alkyl substituted by the radical $OR_5$ or by the radical $SR_5$, $C_3$-$C_6$cycloalkyl, $C_3$-$C_6$cycloalkyl mono- to tri-substituted by $C_1$-$C_4$alkyl or by halogen, $C_2$-$C_5$alkenyl, $C_2$-$C_5$alkynyl or the formyl radical; $R_3$ is $C_1$-$C_4$alkyl, $C_1$-$C_4$alkyl substituted by halogen, cyano or by the radical $OR_5$ or by the radical $SR_5$, $C_3$-$C_6$cycloalkyl or $C_3$-$C_6$cycloalkyl mono- to tri-substituted by $C_1$-$C_4$alkyl or by halogen; $R_4$ is halogen, $C_1$-$C_3$alkyl, $C_1$-$C_2$haloalkyl, $C_1$-$C_3$alkoxy or $C_1$-$C_3$haloalkoxy; $R_5$ is hydrogen, $C_1$-$C_5$alkyl, $C_3$-$C_5$alkenyl, $C_3$-$C_5$alkynyl or the radical $(CH_2)_n$—X—$C_1$-$C_3$alkyl; $R_7$ is —$NH_2$; X is oxygen or sulfur; and n is 1 to 3; including the acid addition salts and metal salt complexes thereof.

5. A compound of formula I according to claim 4, wherein: $R_1$ is phenyl or phenyl mono- to tri-substituted by $R_4$; $R_2$ is hydrogen, $C_1$-$C_5$alkyl, $C_1$-$C_5$alkyl substituted by the radical $OR_5$ or by the radical $SR_5$, $C_3$-$C_6$cycloalkyl, $C_3$-$C_6$cycloalkyl mono- to tri-substituted by $C_1$-$C_4$alkyl or by halogen, $C_2$-$C_5$alkenyl, $C_2$-$C_5$alkynyl or the formyl radical; $R_3$ is $C_1$-$C_4$alkyl, $C_1$-$C_4$alkyl substituted by halogen, cyano or by the radical $OR_5$ or by the radical $SR_5$, $C_3$-$C_6$cycloalkyl or $C_3$-$C_6$cycloalkyl mono- to tri-substituted by $C_1$-$C_4$alkyl or by halogen; $R_4$ is halogen; $R_5$ is hydrogen, $C_1$-$C_5$alkyl, $C_3$-$C_5$alkenyl, $C_3$-$C_5$alkynyl or the radical $(CH_2)_n$—X—$C_1$-$C_3$alkyl; X is oxygen or sulfur; and n is 1 to 3.

6. A compound of formula I according to claim 1, wherein: $R_1$ is phenyl or phenyl mono- to tri-substituted by halogen; $R_2$ is hydrogen, $C_1$-$C_5$alkyl, $C_1$-$C_5$alkyl substituted by the radical $OR_5$ or by the radical $SR_5$, $C_3$-$C_6$cycloalkyl, $C_3$-$C_6$cycloalkyl mono- to tri-substituted by $C_1$-$C_4$alkyl or by halogen, $C_2$-$C_5$alkenyl, $C_2$-$C_5$alkynyl or the formyl radical; $R_3$ is $C_1$-$C_4$alkyl, $C_1$-$C_4$alkyl substituted by halogen, cyano or by the radical $OR_5$ or by the radical $SR_5$, $C_3$-$C_6$cycloalkyl or $C_3$-$C_6$cycloalkyl mono- to tri-substituted by $C_1$-$C_4$alkyl or by halogen; $R_5$ is hydrogen, $C_1$-$C_5$alkyl, $C_3$-$C_5$alkenyl, $C_3$-$C_5$alkynyl or the radical $(CH_2)_n$—X—$C_1$-$C_3$alkyl; X is oxygen or sulfur; and n is 1 to 3.

7. A compound of formula I according to claim 1, wherein: $R_1$ is phenyl or phenyl mono-substituted by chlorine or by fluorine; $R_2$ is $C_1$-$C_5$alkyl, or is $C_1$-$C_2$alkyl substituted by $OR_5$, $C_3$-$C_6$cycloalkyl, $C_3$-$C_6$cycloalkyl mono- to tri-substituted by $C_1$-$C_4$alkyl or by halogen, $C_2$-$C_5$alkenyl, $C_2$-$C_5$alkynyl or the formyl radical; $R_3$ is $C_1$-$C_4$alkyl, $C_1$-$C_4$haloalkyl, $C_3$-$C_6$cycloalkyl or $C_3$-$C_6$cycloalkyl substituted by methyl; and $R_5$ is hydrogen or $C_1$-$C_2$alkyl.

8. A compound of formula I according to claim 7, wherein $R_3$ is: methyl, fluoromethyl, chloromethyl, bromomethyl, $C_3$-$C_6$cycloalkyl or methoxymethyl.

9. A compound of formula I according to claim 1 from the group:
N-(4-fluoromethyl-6-cyclopropylpyrimid-2-yl)-N-phenylhydrazine;
N-(4-methyl-6-cyclopropylpyrimid-2-yl)-N-m-fluorophenylhydrazine;
N-(4-methyl-6-cyclopropylpyrimid-2-yl)-N-p-fluorophenylhydrazine.

10. A compound of formula I according to claim 5 from the group:
N-(4-methyl-6-cyclopropylpyrimid-2-yl)-N-phenylhydrazine; N-(4,6-dimethylpyrimid-2-yl)-N-phenylhydrazine; N-(4-methyl-6-methoxymethylpyrimid-2-yl)-N-phenylhydrazine.

11. A compound of formula I according to claim 1 from the group:
N-(4,6-dimethylpyrimid-2-yl)-N-phenylpropionaldehyde hydrazone;
N-(4,6-dimethylpyrimid-2-yl)-N-phenylisobutyraldehyde hydrazone;
N-(4-methyl-6-methoxymethylpyrimid-2-yl)-N-phenylisobutyraldehyde hydrazone;
N-(4-methyl-6-methoxymethylpyrimid-2-yl)-N-phenylpropionaldehyde hydrazone;
N-(4-methyl-6-cyclopropylpyrimid-2-yl)-N-phenylpropionaldehyde hydrazone;
N-(4-methyl-6-cyclopropylpyrimid-2-yl)-N-phenyl-n-butyraldehyde hydrazone;
N-(4-methyl-6-cyclopropylpyrimid-2-yl)-N-phenylisobutyraldehyde hydrazone;
N-(4-methyl-6-cyclopropylpyrimid-2-yl)-N-phenyltrichloroacetaldehyde hydrazone;
N-(4-methyl-6-cyclopropylpyrimid-2-yl)-N-p-fluorophenylacetaldehyde hydrazone;
N-(4-methyl-6-cyclopropylpyrimid-2-yl)-N-p-fluorophenylisobutyraldehyde hydrazone;
N-(4-methyl-6-cyclopropylpyrimid-2-yl)-N-m-fluorophenylisobutyraldehyde hydrazone;
N-(4,6-dimethylpyrimid-2-yl)-N-phenyl-N'-methylhydrazine;
N-(4,6-dimethylpyrimid-2-yl)-N-phenyl-N'-dimethylhydrazine;
N-(4,6-dimethylpyrimid-2-yl)-N-phenyl-N'-n-propylhydrazine;
N-(4,6-dimethylpyrimid-2-yl)-N-phenyl-N'-isobutylhydrazine;
N-(4-methyl-6-methoxymethylpyrimid-2-yl)-N-phenyl-N'-methylhydrazine;
N-(4-methyl-6-methoxymethylpyrimid-2-yl)-N-phenyl-N'-n-propylhydrazine;
N-(4-methyl-6-methoxymethylpyrimid-2-yl)-N-phenyl-N-dimethylhydrazine;

N-(4-methyl-6-cyclopropylpyrimid-2-yl)-N-phenyl-N'-methylhydrazine;

N-(4-methyl-6-cyclopropylpyrimid-2-yl)-N-phenyl-N'-isobutylhydrazine;

N-(4-methyl-6-cyclopropylpyrimid-2-yl)-N-phenyl-N'-dimethylhydrazine;

N-(4-methyl-6-cyclopropylpyrimid-2-yl)-N-phenyl-N'-diethylhydrazine;

N-(4-methyl-6-cyclopropylpyrimid-2-yl)-N-phenyl-N'-methyl-N'-ethylhydrazine;

N-(4-methyl-6-cyclopropylpyrimid-2-yl)-N-p-fluorophenyl-N'-ethylhydrazine;

N-(4-methyl-6-methoxymethylpyrimid-2-yl)-N-m-fluorophenyl-N'-isopropylhydrazine.

12. A process for the preparation of a compound of formula I according to claim 1, which comprises a) reacting a pyrimidine derivative of formula II

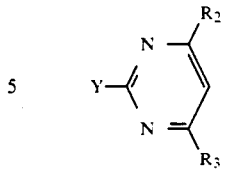

with a phenylhydrazine derivative of formula III

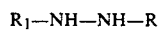

$R_1$—NH—NH—R (III)

in the presence of a base, in an aprotic solvent and at temperatures of $-50°$ to $150°$ C., wherein Y is halogen, the radical $SO_2R_6$ of $N^{\oplus}(CH_3)_3$, $R_6$ is $C_1$–$C_4$alkyl, phenyl or phenyl substituted by methyl or by chlorine and R is hydrogen, $CH(R_8)R_9$, phenyl, $C_1$–$C_5$-alkyl, $C_3$–$C_5$-alkenyl, $C_3$–$C_5$-alkynyl or cyanoalkyl having 2 or 3 carbons in the alkyl radical.

* * * * *